(12) United States Patent
Ruman et al.

(10) Patent No.: US 9,018,434 B2
(45) Date of Patent: Apr. 28, 2015

(54) ABSORBENT ARTICLES WITH INTRICATE GRAPHICS

(75) Inventors: Marcille Faye Ruman, Oshkosh, WI (US); Shannon K. Melius, Appleton, WI (US); Eric Donald Johnson, Larsen, WI (US); Tami L. Kurtz, Oshkosh, WI (US); Marty J. Granius, Menasha, WI (US); Dean M. Wydeven, Appleton, WI (US); Anita M. Gilgenbach, Neenah, WI (US); Aaron D. Schilpp, Appleton, WI (US); Michael Donald Sperl, Waupaca, WI (US); Paula K. DeBruin, Sherwood, WI (US); Thomas Michael Ales, Neenah, WI (US); Joy Patricia Bauman, Neenah, WI (US); Steven Carl Strubbe, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 12/852,192

(22) Filed: Aug. 6, 2010

(65) Prior Publication Data

US 2012/0035563 A1 Feb. 9, 2012

(51) Int. Cl.
A61F 13/42 (2006.01)

(52) U.S. Cl.
CPC ..................... *A61F 13/42* (2013.01)

(58) Field of Classification Search
USPC .................. 604/358, 361, 385.01; D24/125
See application file for complete search history.

(56) References Cited

U.S. PATENT DOCUMENTS

| | | | |
|---|---|---|---|
| 3,675,654 A | 7/1972 | Baker et al. | |
| 3,731,685 A | 5/1973 | Eidus | |
| 4,022,211 A * | 5/1977 | Timmons et al. | 604/361 |
| 4,100,324 A | 7/1978 | Anderson et al. | |
| 4,192,311 A | 3/1980 | Felfoldi | |
| 4,292,916 A | 10/1981 | Bradley et al. | |
| 4,327,731 A | 5/1982 | Powell | |
| 4,366,241 A | 12/1982 | Tom et al. | |

(Continued)

FOREIGN PATENT DOCUMENTS

| | | |
|---|---|---|
| DE | 10 2007 006 230 A1 | 8/2008 |
| JP | 4143876 A | 5/1992 |

(Continued)

OTHER PUBLICATIONS

U.S. Appl. No. 12/503,364, filed Jul. 15, 2009.

(Continued)

*Primary Examiner* — Jackie T Ho
*Assistant Examiner* — Kathryn E Ditmer
(74) *Attorney, Agent, or Firm* — Dority & Manning, P.A.

(57) ABSTRACT

Absorbent articles are disclosed that have been printed with active graphics alone or in combination with permanent graphics to create a wetness indicator. Different active graphic compositions and/or permanent graphic compositions are combined so as to make the wetness indicator very prominent on the article. In addition, when the absorbent article is wetted, the active graphics undergo a change that is easily noticed by the wearer or the caregiver for the wearer. In one embodiment, for instance, active graphics are positioned within a distinctive frame. The frame focuses a person's attention onto the active graphics. The active graphics fill most of the surface area of the frame such that when the absorbent article is wetted, a clearly noticeable change occurs.

17 Claims, 6 Drawing Sheets

(56) References Cited

U.S. PATENT DOCUMENTS

| | | | |
|---|---|---|---|
| 4,734,238 A | 3/1988 | Sugimori et al. |
| 4,812,053 A | 3/1989 | Bhattacharjee |
| 4,903,254 A | 2/1990 | Haas |
| 4,931,051 A | 6/1990 | Castello |
| 4,940,464 A | 7/1990 | Van Gompel et al. |
| 4,987,849 A | 1/1991 | Sherman |
| 5,006,711 A | 4/1991 | Hamashima et al. |
| 5,045,283 A | 9/1991 | Patel |
| 5,053,339 A | 10/1991 | Patel |
| 5,058,088 A | 10/1991 | Haas et al. |
| 5,089,548 A | 2/1992 | Zimmel et al. |
| 5,130,290 A | 7/1992 | Tanimoto |
| 5,284,703 A | 2/1994 | Everhart et al. |
| 5,350,624 A | 9/1994 | Georger et al. |
| 5,350,625 A | 9/1994 | Peterson et al. |
| 5,352,582 A | 10/1994 | Lichtenwalter et al. |
| 5,389,093 A | 2/1995 | Howell |
| 5,468,236 A | 11/1995 | Everhart et al. |
| 5,486,166 A | 1/1996 | Bishop et al. |
| 5,490,846 A | 2/1996 | Ellis et al. |
| 5,645,542 A | 7/1997 | Anjur et al. |
| 5,726,435 A | 3/1998 | Hara et al. |
| 5,766,389 A | 6/1998 | Brandon et al. |
| 5,820,973 A | 10/1998 | Dodge, II et al. |
| 5,854,148 A | 12/1998 | Asada et al. |
| 5,954,512 A | 9/1999 | Fruge |
| 5,989,923 A | 11/1999 | Lowe et al. |
| 6,200,765 B1 | 3/2001 | Murphy et al. |
| 6,294,392 B1 | 9/2001 | Kuhr et al. |
| 6,297,424 B1 | 10/2001 | Olson et al. |
| 6,307,119 B1 | 10/2001 | Cammarota et al. |
| 6,362,389 B1 | 3/2002 | McDowall et al. |
| 6,436,651 B1 | 8/2002 | Everhart et al. |
| 6,596,918 B1* | 7/2003 | Wehrle et al. | 604/361 |
| 6,610,386 B2 | 8/2003 | Williams et al. |
| 6,635,797 B2 | 10/2003 | Olson et al. |
| 6,645,190 B1 | 11/2003 | Olson et al. |
| 6,710,221 B1 | 3/2004 | Pierce et al. |
| 6,713,660 B1 | 3/2004 | Roe et al. |
| 6,722,886 B2 | 4/2004 | Blumberg |
| 6,772,708 B2 | 8/2004 | Klofta et al. |
| 6,786,412 B2 | 9/2004 | Shimizu |
| 6,856,249 B2 | 2/2005 | Strubbe et al. |
| 6,904,865 B2 | 6/2005 | Klofta et al. |
| 6,997,384 B2 | 2/2006 | Hara |
| 7,053,029 B2 | 5/2006 | MacDonald et al. |
| 7,159,532 B2 | 1/2007 | Klofta et al. |
| 7,195,165 B2 | 3/2007 | Kesler et al. |
| 7,282,349 B2 | 10/2007 | Lye et al. |
| 7,300,770 B2 | 11/2007 | Martin et al. |
| 7,306,764 B2 | 12/2007 | Mody |
| 7,321,315 B2 | 1/2008 | Brumm et al. |
| 7,332,642 B2 | 2/2008 | Liu |
| 7,355,090 B2 | 4/2008 | Ales et al. |
| 7,399,608 B2 | 7/2008 | MacDonald et al. |
| 7,413,550 B2 | 8/2008 | MacDonald et al. |
| 7,476,443 B2 | 1/2009 | Huang et al. |
| 7,531,319 B2 | 5/2009 | Martin et al. |
| 7,561,989 B2 | 7/2009 | Banks et al. |
| 7,582,485 B2 | 9/2009 | Boga et al. |
| 7,592,020 B2 | 9/2009 | Boga et al. |
| 7,674,747 B1 | 3/2010 | Long |
| 7,687,245 B2 | 3/2010 | Lye et al. |
| 7,718,844 B2 | 5/2010 | Olson |
| 7,722,357 B2 | 5/2010 | Payette-Hebert et al. |
| 7,727,513 B2 | 6/2010 | MacDonald et al. |
| 7,750,202 B2 | 7/2010 | Niemeyer |
| 7,829,181 B2 | 11/2010 | MacDonald et al. |
| 7,837,663 B2 | 11/2010 | MacDonald et al. |
| 7,879,744 B2 | 2/2011 | Seidling et al. |
| 2001/0031954 A1 | 10/2001 | Jordan et al. |
| 2004/0064113 A1* | 4/2004 | Erdman | 604/361 |
| 2004/0078219 A1 | 4/2004 | Kaylor et al. |
| 2005/0065489 A1 | 3/2005 | Driskell et al. |
| 2005/0101841 A9 | 5/2005 | Kaylor et al. |
| 2005/0112085 A1 | 5/2005 | MacDonald et al. |
| 2005/0137542 A1 | 6/2005 | Underhill et al. |
| 2005/0148961 A1* | 7/2005 | Sosalla et al. | 604/361 |
| 2005/0217791 A1 | 10/2005 | Costello et al. |
| 2005/0234414 A1* | 10/2005 | Liu | 604/361 |
| 2005/0252967 A1 | 11/2005 | Kesler et al. |
| 2006/0069360 A1 | 3/2006 | Long et al. |
| 2006/0069361 A1* | 3/2006 | Olson | 604/361 |
| 2006/0149197 A1 | 7/2006 | Niemeyer |
| 2006/0223052 A1 | 10/2006 | MacDonald et al. |
| 2006/0224443 A1 | 10/2006 | Soza et al. |
| 2006/0229577 A1 | 10/2006 | Roe et al. |
| 2006/0229578 A1* | 10/2006 | Roe et al. | 604/361 |
| 2007/0071320 A1 | 3/2007 | Yada |
| 2007/0079748 A1 | 4/2007 | Ahmed et al. |
| 2007/0138286 A1 | 6/2007 | Kamijoh et al. |
| 2007/0142263 A1 | 6/2007 | Stahl et al. |
| 2007/0156106 A1* | 7/2007 | Klofta et al. | 604/361 |
| 2007/0199994 A1 | 8/2007 | Cattrone et al. |
| 2007/0259997 A1 | 11/2007 | Bakker et al. |
| 2007/0282286 A1 | 12/2007 | Collins et al. |
| 2008/0057534 A1 | 3/2008 | Martin et al. |
| 2008/0091156 A1* | 4/2008 | Maldonado et al. | 604/361 |
| 2008/0145316 A1 | 6/2008 | MacDonald et al. |
| 2008/0147030 A1 | 6/2008 | Nhan et al. |
| 2008/0147031 A1 | 6/2008 | Long et al. |
| 2008/0243015 A1 | 10/2008 | MacDonald et al. |
| 2008/0276379 A1 | 11/2008 | MacDonald et al. |
| 2008/0277621 A1 | 11/2008 | MacDonald et al. |
| 2008/0294134 A1* | 11/2008 | Schroer, Jr. | 604/361 |
| 2009/0005748 A1 | 1/2009 | Ales et al. |
| 2009/0050700 A1 | 2/2009 | Kamijoh et al. |
| 2009/0062757 A1 | 3/2009 | Long et al. |
| 2009/0062764 A1 | 3/2009 | MacDonald et al. |
| 2009/0111088 A1 | 4/2009 | Martin et al. |
| 2009/0137172 A1 | 5/2009 | Huang et al. |
| 2009/0142275 A1 | 6/2009 | Phillips et al. |
| 2009/0143516 A1 | 6/2009 | MacDonald et al. |
| 2009/0143754 A1 | 6/2009 | Boga et al. |
| 2009/0155753 A1 | 6/2009 | Ales et al. |
| 2009/0157025 A1 | 6/2009 | Song et al. |
| 2009/0171307 A1 | 7/2009 | Chang et al. |
| 2009/0221061 A1 | 9/2009 | Martin et al. |
| 2009/0221980 A1 | 9/2009 | Mosbacher et al. |
| 2009/0247979 A1 | 10/2009 | Sosalla et al. |
| 2009/0275908 A1 | 11/2009 | Song |
| 2009/0287173 A1 | 11/2009 | Sosalla et al. |
| 2009/0326491 A1 | 12/2009 | Long et al. |
| 2010/0164733 A1 | 7/2010 | Ales et al. |
| 2010/0168694 A1 | 7/2010 | Gakhar et al. |
| 2011/0015063 A1 | 1/2011 | Gil et al. |
| 2011/0015597 A1 | 1/2011 | Gil et al. |
| 2011/0106035 A1* | 5/2011 | Arora et al. | 604/367 |

FOREIGN PATENT DOCUMENTS

| | | | |
|---|---|---|---|
| JP | 2003 058759 A | 2/2003 |
| JP | 2006 249638 A | 9/2006 |
| JP | 2009 280946 A | 12/2009 |
| WO | WO 96/08788 A1 | 3/1996 |
| WO | WO 00/37009 A2 | 6/2000 |
| WO | WO 00/65348 A2 | 11/2000 |
| WO | WO 2004/084765 A2 | 10/2004 |
| WO | WO 2008/072116 A1 | 6/2008 |
| WO | WO 2010/015881 A1 | 2/2010 |

OTHER PUBLICATIONS

U.S. Appl. No. 12/503,380, filed Jul. 15, 2009.
Search Report and Written Opinion for PCT/IB2011/052904 dated Mar. 9, 2012, 12 pages.

* cited by examiner

ABSORBENT ARTICLES WITH INTRICATE GRAPHICS

BACKGROUND

Many different types of absorbent products exist that are designed to be worn or otherwise associated with the body for absorbing body fluids. Such absorbent products can include, but are not limited to, diapers, training pants, adult incontinence products, feminine hygiene products, bed liners, bandages, and the like. In some embodiments the absorbent articles contain a cover material, a liner, and an absorbent structure positioned in between the outer cover and the liner. The absorbent structure typically contains superabsorbent particles. Many absorbent articles, especially those sold under the trade name HUGGIES® by the Kimberly-Clark Corporation, are so efficient at absorbing liquids that it is sometimes difficult for the wearer or the caregiver to tell whether or not the absorbent article has been insulted with a body fluid, such as urine.

Accordingly, various types of moisture or wetness indicators have been suggested for use in absorbent articles. The wetness indicators can be used for different purposes. For instance, the wetness indicators can be designed to assist parents or attendants by helping them identify a wet diaper condition early on.

Wetness indicators can also be used as a training aid for small children during the toilet training process. For example, wetness indicators can be designed to discourage small children from wetting the absorbent article and to encourage small children to use a toilet like an adult.

Wetness indicators used in the past have included wetness indicator graphics that have been printed on the absorbent article. Absorbent articles having wetness indicator graphics, for instance, are described in U.S. Pat. No. 6,297,424, in U.S. Pat. No. 6,710,221, and in U.S. Patent Application Publication No. 2006/0149197, which are all incorporated herein by reference. Although the above patents have provided great advances in the art, further improvements are still needed.

For instance, prior commercial wetness indicator graphics have been created using water soluble inks that dissolve when wet. Thus, once contacted with urine, the graphics smear and fade indicating that the absorbent article is wet. Unfortunately, however, graphics produced with water soluble inks have been somewhat limited in size, shape, position, line width, color and the like in order to ensure sufficient fading when contacted with urine.

In addition, the fading graphics have been typically placed against a white background. Such fading graphics have been found to be somewhat difficult to discern by either the child wearing the absorbent article or by a caregiver or attendant. Thus, a need currently exists for further improvements in wetness indicator graphics that are designed to better indicate that the absorbent article has been wetted.

SUMMARY

The present disclosure is generally directed to absorbent articles with visual wetness indicators. The wetness indicator generally comprises graphics that are printed with active graphic compositions that change when contacted with urine and permanent graphic compositions that do not change when contacted with urine. As will be described in greater detail below, the various embodiments of the present disclosure provide for an improved noticeable change in appearance when the absorbent article changes from dry to a wet condition. In particular, the embodiments of the present disclosure allow the wearers of the absorbent article or allow caregivers to more readily notice when the absorbent article has been wetted.

In various embodiments, for instance, the active graphics present on the absorbent article are relatively large in size, especially in relation to many prior art constructions. Greater amounts of active graphic composition are applied to the absorbent articles to make the active graphics easily visible. Ultimately, the size of the active graphics is maximized in conjunction with dramatic color changes. For instance, a dramatic change in appearance occurs when a relatively large active graphic changes from one or more colors to clear.

Prior to describing the embodiments of the present disclosure in detail, the following are definitions of various terms.

The term "active graphic" as used herein refers to an appearing graphic, a fading graphic, a color changing graphic or a combination thereof. The term "appearing graphic" is used herein to refer to a graphic that becomes visible (appears) or becomes significantly more visible when exposed to a body exudate. Conversely, the term "fading graphic" is used herein to refer to a graphic that becomes invisible (disappears) or significantly less visible when exposed to a body exudate, such as urine, fecal matter, a vaginal secretion or a nasal discharge.

In particular embodiments, the active graphic can comprise a fading graphic which is formed from an ink that is soluble in aqueous solutions such as a body exudate. The ink is positioned in the absorbent article so that it becomes wet and dissolves when the product is insulted with a liquid. Once dissolved, the ink washes away from the outer cover and is obscured by the outer cover. As a result, the active graphic seems to disappear from view.

Suitable urine-soluble inks are available from a variety of commercial vendors, such as Sun Chemical Corp. of Philadelphia, Pa., USA under the trade designation AQUA DESTRUCT. Particular urine-soluble compositions are disclosed in U.S. Pat. No. 4,022,211 issued May 10, 1977 to Timmons et al., which is incorporated herein by reference. The ink color can be selected to provide a pleasing appearance and graphic impact, including fading rapidly upon contact with liquid.

The active graphic can also comprise a color changing graphic which is formed from a composition such as an ink or adhesive that changes color when exposed to an aqueous solution such as urine. A color change composition can be adapted to blend in with a background or surrounding color, either before or after exposure to the aqueous solution or to undergo a more noticeable color change. Suitable compositions of this color-change type are available from a variety of commercial vendors, such as a pH-change/color-change hot melt adhesive available from Findley Adhesives, Inc. of Wauwatosa, Wis., USA. Alternatively, the active graphic can comprise pH sensitive inks, fugitive inks, colored absorbent particles, hydratable salts, moisture sensitive films, enzymes, heat sensitive inks and dyes, or the like.

In one embodiment, a color changing active graphic composition may comprise a matrix-forming component, a colorant, a surfactant and a pH adjuster. The matrix-forming component may be a water-insoluble, film-forming polymer or an ink base, such as a flexographic varnish having an organic solvent base. The colorant can be a pH indicator, such as a charged pH indicator, capable of changing color in response to the presence of a fluid. The surfactant may include a charged surfactant that attracts the colorant or a combination of charged surfactants that attract the colorant and a neutral surfactant. The pH adjuster may include a low molecular weight organic acid and a high molecular weight organic acid.

The matrix-forming component may comprise, for instance, an acrylate/acrylamide copolymer, a polyurethane adhesive, methylcellulose, and/or copolymers of vinylpyrrolidone and dimethylaminopropyl methacrylamide. Such color changing compositions are disclosed, for instance, in U.S. patent application Ser. No. 12/503,364 or 12/503,380, which are incorporated herein by reference.

In addition to ink compositions, the active graphic can also comprise a dye, an adhesive, or any other suitable chemical.

In contrast to active graphics, the term "permanent graphic" is used herein to refer to a graphic that does not substantially change its degree of visibility when the absorbent article is insulted with urine in simulated use conditions. The change in visibility of a graphic or a portion of a graphic can be determined based on a person's observation of the graphic before and after the article containing the graphic is exposed to liquid. For purposes hereof, an article is exposed to liquid by immersing the article completely in an aqueous solution containing 0.9 weight percent sodium chloride, used at room temperature ($\cong 23°$ C.), for a period of twenty minutes. After 20 minutes the product is removed from the aqueous solution and placed on a TEFLON™ coated fiberglass screen having 0.25 inch openings, which is commercially available from Taconic Plastics Inc., Petersberg, N.Y., USA, which in turn is placed on a vacuum box and covered with a flexible rubber dam material. A vacuum of 3.5 kilopascals (0.5 pounds per square inch) is drawn in the vacuum box for a period of 5 minutes, after which the article is removed and observed. The person with normal or corrected vision of 20-20 should make the observations from a distance of 1 meter in an environment providing 30 footcandles (320 Lux) of illumination. Changes in the visibility of the graphic should be identified, and distinguished where necessary from changes in the color of other materials such as fluff pulp within an absorbent assembly. Desirably, the permanent graphic can be configured so that the entire graphic also does not substantially change its appearance, size or shape when the product is insulted with liquid or exposed to the environment.

The graphics of the absorbent article can be constructed to provide a story line involving a permanent character graphic and an active object graphic. The term "character graphic" is used herein to refer to a graphic containing an anthropomorphous image, and in particular an image having or suggesting human form or appearance which ascribes human motivations, characteristics or behavior to inanimate objects, animals, natural phenomena, cartoon characters, or the like. The character graphics can comprise permanent graphics, active graphics, or both permanent and active graphics.

The character graphic can desirably comprise a portion of the entire absorbent article graphic that sets up a theme for the illustrated scene. As such, the character graphic can provide an opportunity for educational interaction between the child and the parent or caregiver. More specifically, the parent or caregiver can use the graphic story-line to make up a game or story for the purpose of toilet training progress.

Suitable character graphics can include animals, people, inanimate objects, natural phenomena, cartoon characters, or the like that can or can not be provided with human features such as arms, legs, facial features or the like. For purposes of enhanced toilet training, it may be desirable for the character graphic to be familiar to the child, such as an identifiable cartoon character. The character graphics should at least be a type that the child can relate to, examples of which could include animals, toys, licensed characters, or the like. Character graphics can be made more personable and friendly to the child by including human-like features, human-like expressions, apparel, abilities, or the like. By way of illustration, an animal character graphic can be shown smiling, wearing clothing, playing sports, fishing, driving, playing with toys, or the like. In particular embodiments, the character graphic can desirably be created to project an appearance that could be described as friendly, positive, non-intimidating, silly, independent, inspirational, active, expressive, dauntless and/or persevering.

In general, absorbent articles made in accordance with the present disclosure contain graphics comprising multiple images, objects and/or characters. All of the graphics can be assembled together on the absorbent article so as to present an integrated look that depicts a scene. In addition to characters and other images as described above, the scene can include a framing device, outlines, a background, a foreground, and one or more silhouettes.

A "framing device" generally refers to a substantially continuous border for enclosing an image. The framing device may, for instance, completely surround a single image or multiple images or may substantially surround an image (such as at least about 90% surrounded). The framing device may also intersect the active graphics. For instance, in one embodiment, the framing device may substantially surround one active graphic while intersecting another active graphic. A product may contain a single framing device or multiple framing devices. The framing device is made from graphics or from white space and may itself comprise an object or be part of a larger image or character. The framing device may be interrelated with any active graphics associated with the framing device. The framing device is not part of leg bands or seams that are present on the article whether the leg bands or seams are printed on the article or are actual functional elements of the article. A framing device also does not include a break or space in the background of a scene depicted on the article. The framing device may define an inner perimeter and an outer perimeter. The distance between the inner perimeter and the outer perimeter can, for instance, be greater than 0.5 mm, such as greater than 2 mm, such as greater than 3 mm, such as greater than 4 mm, such as greater than 5 mm. The distance between the inner perimeter and the outer perimeter can also be less than about 50 mm, such as less than about 25 mm, such as less than about 10 mm. In one embodiment, the distance between the inner perimeter and the outer perimeter can be from about 1 mm to about 10 mm, such as from about 3 mm to about 7 mm.

An "outline", on the other hand, refers to the lines by which the essential features or main aspects of an image, object or character is defined or bound. In one embodiment, for instance, a character appearing on an absorbent article may include an outline made from permanent graphics or from white space. Within the outline, the character may be colored using active graphics.

As used herein, the "background" of a scene is the surface against which represented objects and forms are perceived or depicted. The background is situated behind the location of an image or object. Each scene includes a background. In addition, various elements within the scene may also include a background.

As used herein, the "foreground" describes the location of an image or object which is situated in front of something. As understood by one skilled in the art, an object may be both in the foreground and the background.

A "silhouette" is a representation of the general shape of an object, image or character without the essential features or main aspects of the object filled in. The silhouette, for instance, excludes the graphic details or elements intended to show the dimensionality or recognition of the image or character such as facial features, clothing details, flower petals, and the like. A silhouette may also comprise a dark image outlined against a lighter background or vice versa.

The present disclosure, as described above, can be directed to applying graphics to an absorbent article including a surface, such as an interior or exterior surface. The surface can have a "printable surface area" which is defined as the surface area of a rectangle which has a length measured from the front edge of the absorbent article to the back edge of the absorbent article and has a width measured as the narrowest portion of the surface, such as the outer cover, which is usually within the crotch region. It should be understood that the permanent and active graphics contained on an absorbent article may have a width that is greater than the width of the printable surface area as defined.

As used herein, the "active graphic surface area" refers to the surface area upon which the active graphic composition has been applied. The "active graphic perimeter surface area", on the other hand, refers to the area defined by the perimeter of the outer most elements of the active graphic and may include areas within the perimeter where an active graphic composition has not been applied.

The outer cover can also include "white space". White space is defined as the predominate color of the surface of the absorbent article. The white space, for instance, may be the color of the material used to create a surface of the absorbent article prior to being treated with any printed graphics. For example, the white space may comprise the natural color of the material used to form a surface of the absorbent article. In one embodiment, the white space present on the absorbent article is white in color and has a white appearance. The white space can be formed from a non-printed area on a substrate or can comprise an area that has been printed or treated with a pigment or ink if it is the predominant color. In one embodiment of the present disclosure, the active graphics fade, disappear, turn clear, or turn the same color as the white space which increases the white space on the outer cover. Alternatively, the active graphics can turn from the white space color to another color thus decreasing the white space on the outer cover.

In one embodiment, the present disclosure is directed to an absorbent article comprising an outer cover having an interior surface and an exterior surface. An absorbent structure is positioned adjacent to the interior surface of the outer cover. In one embodiment, the absorbent article can further include a liquid permeable liner. The absorbent structure can be positioned in between the outer cover and the liquid permeable liner.

In accordance with the present disclosure, the absorbent article includes at least one active graphic incorporated into the absorbent article such that the active graphic is visible from the exterior surface of the outer cover. The at least one active graphic can be substantially surrounded or completely surrounded by a framing device or outline.

In accordance with the present disclosure, in one embodiment, the at least one active graphic can have a surface area of greater than about 800 mm$^2$, such as greater than about 1000 mm$^2$. In one embodiment, one or more active graphics can occupy all of the surface area of the outer cover, such as the entire printable surface area of the outer cover. The active graphic in various embodiments may have a surface area of less than about 140,000 mm$^2$, such as less than about 45,000 mm$^2$, such as less than about 20,000 mm$^2$, such as less than about 8000 mm$^2$ depending on the type and size of the article (adult article versus child article).

As described above, the outer cover may define a printable surface area. In one embodiment, the active graphic may occupy greater than 1% of the printable surface area of the outer cover, such as greater than about 1.2%, such as greater than about 1.4% of the printable surface area of the outer cover.

The absorbent article can generally be divided into three regions. For instance, the absorbent article can include a front region, a back region, and a crotch region in between the front region and the back region. In one particular embodiment, each of the regions can have substantially the same length in the longitudinal direction. The framing device or outline that substantially surrounds the active graphic can be primarily located in the crotch region or completely located in the crotch region. As used herein, the term "primarily" means that more than 50% of the framing device or outline be located in the crotch region.

In an alternative embodiment, the framing device or outline can be primarily located in the front region or completely located in the front region. In general, the framing device, outline and/or active graphics can be positioned at any suitable location on the absorbent article. The location of various active graphics on absorbent articles, for instance, are shown and/or described in U.S. Pending Application Publication No. 2006/0149197 or in U.S. Patent Application Publication No. 2009/0062757, which are incorporated herein by reference.

The exterior surface or the interior surface of the absorbent article may also be divided into two halves in the longitudinal direction. For instance, the absorbent article can include a front half and a back half. The front half extends from the front edge of the article to the midpoint of the article between the front edge and the back edge. The back half of the absorbent article, on the other hand, may extend from the back edge of the article to the midpoint. The front half and the back half can each include a printable surface area that is generally one half of the printable surface area of the entire exterior surface or interior surface. In many applications, the active graphics and/or permanent graphics can all be present only on the front half or only on the back half of the absorbent article.

The at least one active graphic contained within the outline or framing device can be comprised of an active graphic composition that undergoes a change when contacted with a body fluid, such as urine. For instance, the active graphic composition may produce a graphic that becomes less visible when contacted with urine, becomes more visible when contacted with urine, or changes color when contacted with urine. In one embodiment, the active graphic composition may change from a color to clear when contacted with urine. In an alternative embodiment, the active graphic composition may undergo a shade change when contacted with urine. As described above, however, the outline or framing device is comprised of a permanent graphic or of white space. The outline or framing device makes the active graphic much more noticeable, especially at the dimensions described above. In this manner, the wetness indicator is easily discernible by either the wearer or caregiver.

In one embodiment, in order to further enhance the ability of the graphics to serve as a wetness indicator, the one or more active graphics contained within the framing device or the outline occupy a substantial portion of the surface area defined by the framing device or outline. For instance, the framing device or outline can have an inner perimeter that defines a surface area therein. In accordance with the present disclosure, the at least one active graphic occupies at least about 35% of the surface area within the inner perimeter. For instance, in one embodiment, the one or more active graphics can occupy at least about 30%, such as at least about 60%, such as at least about 70%, such as at least about 80% of the surface area defined by the inner perimeter. In one particular embodiment, the surface area defined by the inner perimeter can be completely occupied by the one or more active graphics. In this manner, when urine contacts the active graphics, a significant change in appearance occurs on the absorbent article.

In one embodiment, at least a portion of the framing device or the outline overlaps at least a portion of the active graphic. Having some overlap between the features not only improves print registration but can also improve the appearance when either dry or wetted.

The framing device that surrounds the active graphic can be integrated into the scene displayed on the absorbent article. For instance, the framing device can comprise an object, image or character that is consistent with the storyline of the overall scene. In one embodiment, for instance, the framing device and the active graphic may combine together to form a single image when dry and/or when wet.

The framing device itself can be very prominent on the absorbent article. The framing device, for instance, may define an inner perimeter and an outer perimeter. The surface area of the inner perimeter may comprise greater than about 4.5% of the printable surface area of the outer cover (such as greater than about 9% of the printable surface area of the front half of the outer cover), such as greater than about 5% of the printable surface area of the outer cover (such as greater than about 10% of the printable surface area of the front half of the outer cover), such as greater than about 7% of the printable surface area of the outer cover (such as greater than about 14% of the printable surface area of the front half of the outer cover), such as even greater than about 9% of the printable surface area of the outer cover (such as greater than about 18% of the printable surface area of the front half of the outer cover).

The surface area defined by the outer perimeter of the framing device may occupy greater than about 5% of the printable surface area of the outer cover (such as greater than about 10% of the printable surface area of the front half of the outer cover), such as greater than about 7.5% of the printable surface area of the outer cover (such as greater than about 15% of the printable surface area of the front half of the outer cover), such as greater than about 10% of the printable surface of the outer cover (such as greater than about 20% of the printable surface area of the front half of the outer cover).

The manner in which the active graphics and/or permanent graphics are incorporated into the absorbent article can vary depending upon the particular application. In one embodiment, for instance, the active graphics can be disposed on the interior surface of the outer cover, while the permanent graphics can be disposed on the exterior surface of the outer cover. Placing the active graphics on the interior surface of the outer cover ensures that the active graphics come into contact with urine when the absorbent article is insulted. In one embodiment, the outer cover may include a liquid permeable outer layer and a liquid impermeable inner layer. The at least one active graphic can be disposed on the surface of the inner layer that forms the interior surface of the outer cover. Permanent graphics, such as a framing device or outline, on the other hand, may be disposed on the opposite surface of the inner layer.

In one embodiment, the active graphics present on the absorbent article may fade, disappear, turn clear or turn into a white color such that the amount of white space on a surface of the absorbent article increases or decreases when the active graphics are activated. In one embodiment, for instance, the outer cover of the absorbent article may define an initial amount of white space and, once the active graphics are activated, the white space on the outer cover may increase or decrease by greater than about 15%, such as greater than about 20%, such as greater than about 40%, such as greater than about 50%, such as even greater than about 60%.

In one embodiment, various elements can be combined to produce a wetness indicator that includes permanent graphics and active graphics. For instance, at least one active graphic can be substantially surrounded by a framing device in addition to an outline. In addition, the active graphic may be placed on a background color. The background color itself can be an active graphic or can be a permanent graphic.

In an alternative embodiment, the present disclosure is directed to an absorbent article including an outer cover and an absorbent structure positioned adjacent to an interior surface of the outer cover. In accordance with the present disclosure, the absorbent article includes an active graphic disposed on the outer cover. The active graphic is formed by applying an active graphic composition to the outer cover in a manner that forms treated areas and untreated areas. The untreated areas can form a visible image on the outer cover. The visible image may comprise, for instance, an object or character. When the active graphic is contacted with urine, however, the active graphic disappears or changes color in a manner that causes the at least one image to become substantially invisible.

In yet another alternative embodiment of the present disclosure, an active graphic is disposed on the absorbent article that is surrounded by a background color. When the absorbent article is in a dry state, the active graphic is substantially invisible. For instance, in one embodiment, the active graphic can be substantially the same color as the background color. When the active graphic is contacted with urine, however, the active graphic becomes visible from the exterior surface of the outer cover. For instance, in one embodiment, the active graphic may fade or disappear leaving an image. Alternatively, the active graphic may change color thereby becoming visible and prominent.

In another embodiment of the present disclosure, the absorbent article includes a wetness indicator that comprises a gauge-like graphic. The gauge-like graphic, for instance, may comprise a framing device surrounding a guage element or a plurality of gauge elements. The gauge elements comprise an active graphic that change color, which includes changing the shade of color, or change from visible to invisible when contacted with a body fluid. In one embodiment, the gauge elements may comprise one or more columns of bars or dots.

In one embodiment, the gauge-like graphic may be relatively small and not integrated into the overall scene depicted on the absorbent article. By being relatively small in size, the gauge-like graphic may provide some discretion to the user. For instance, the gauge-like graphic may be applied to an adult incontinence product and may only be easily recognized by the user.

For instance, in one embodiment, the gauge elements contained within the gauge-like graphic may have a surface area of less than about 150 mm$^2$, such as less than about 120 mm$^2$, such as less than 90 mm$^2$. The gauge elements may occupy greater than about 20 mm$^2$, such as greater than about 50 mm$^2$, such as greater than about 70 mm$^2$.

The framing device that surrounds the gauge elements may have an inner perimeter that defines a surface area. The gauge elements may occupy less than about 20% of the inner perimeter surface area, such as less than about 18% of the inner surface area, such as less than about 15% of the inner surface area.

As described above, the outer cover of the absorbent article defines a total printable surface area. The gauge elements can occupy less than about 0.2% of the perimeter surface area of the outer cover, such as less than about 0.15% of the printable surface area, such as less than about 0.12% of the printable surface area.

The framing device of the gauge-like graphic may also have an outer perimeter that defines a surface area therein. The surface area of the outer perimeter may generally occupy less than about 4% of the printable surface area of the outer cover. For instance, the surface area of the outer perimeter of the framing device may occupy less than about 3%, such as less than about 2% of the printable surface area of the outer cover.

Other features and aspects of the present disclosure are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
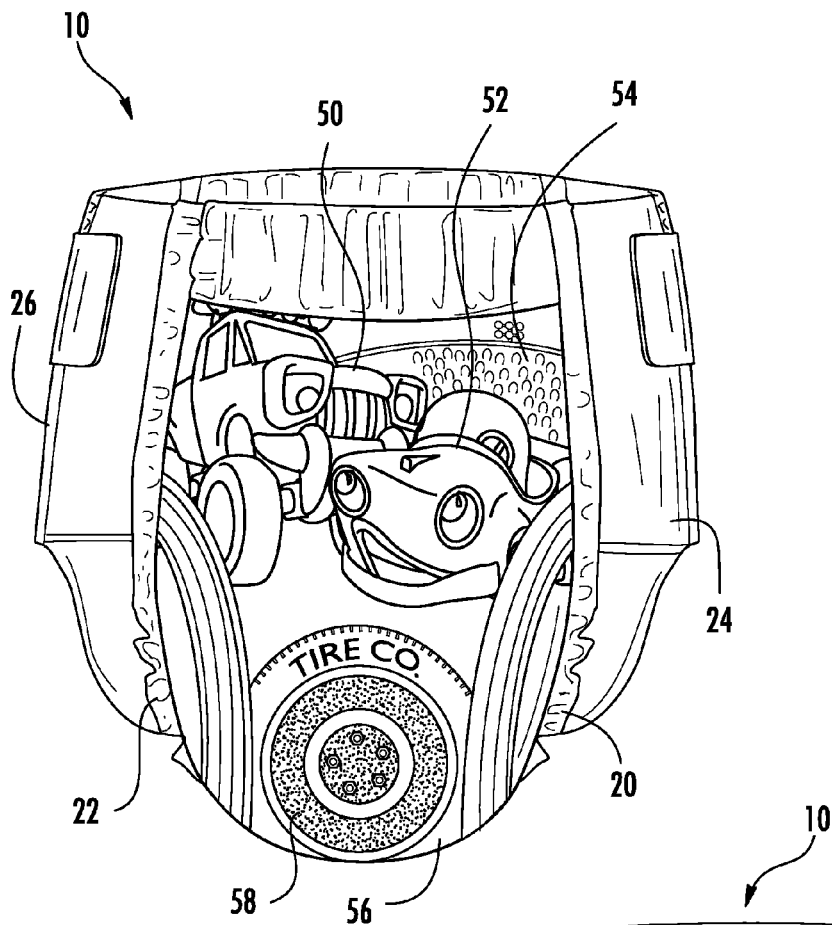
FIGS. 1, 2 and 3 are plan views of one embodiment of an absorbent article made in accordance with the present disclosure including a wetness indicator.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to absorbent articles incorporating a wetness indicator. In accordance with the present disclosure, the wetness indicator includes a combination of active graphics and permanent graphics. In one embodiment, for instance, the active graphics and permanent graphics may be interrelated to display an overall scene with a common storyline. The permanent graphics are used to accentuate the active graphics for providing a very prominent change when the absorbent article is wetted. In this manner, the wearer or caregiver can instantly ascertain when the absorbent article has been insulted with a body fluid, such as urine.

In one embodiment, for instance, the scene depicted upon the absorbent article provides an integrated, one-piece look that can be consistent with a background color that covers substantially the entire outer cover and side panels. The absorbent article can include an intuitive wetness indicating graphic that, in one embodiment, eliminates a substantial amount of white area in the crotch region of the absorbent article and highlights the location of the active graphic when the product is dry. When wetted, the active graphic offers a dramatic visual change without compromising the integrated appearance of the product. The wetness indicator of the present disclosure can be incorporated into all sizes of absorbent articles and can be designed to appeal to a certain gender.

Figure 2:
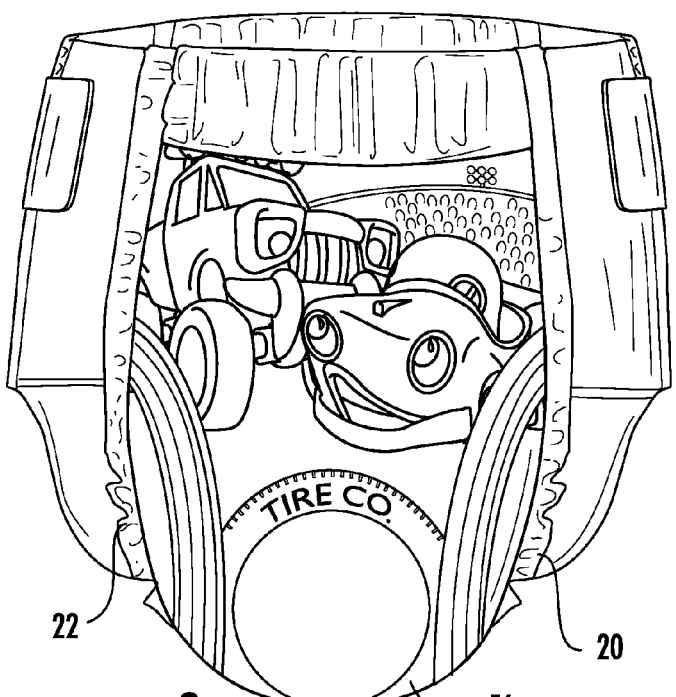
Figure 3:
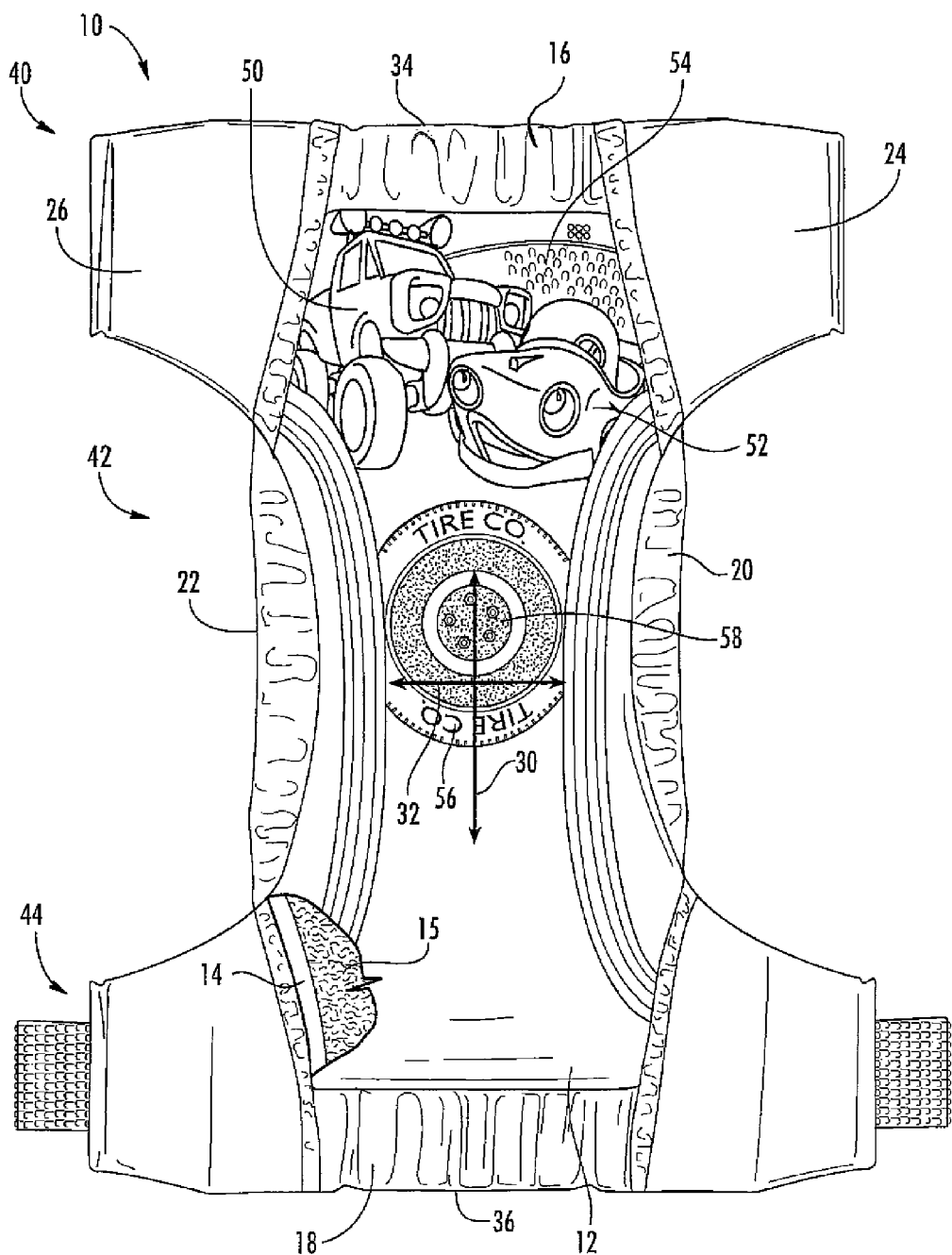

Referring to FIGS. 1 through 3, for instance, one embodiment of an absorbent article 10 made in accordance with the present disclosure is shown. In the figures, a child's training pant is generally shown. It should be understood, however, that the inventive concepts described herein can be applied to any suitable absorbent article, such as a diaper, an adult incontinence product, a feminine hygiene product or the like.

In the figures, the active graphics and permanent graphics are shown to be visible from an exterior surface of the absorbent article, such as by being applied to the outer cover. It should be understood, however, that the graphics may also be applied so as to be visible from an interior surface of the article. For instance, when applied to a feminine hygiene product, the graphics may more appropriately be placed to be visible from the interior surface which is adjacent to the body of the wearer. In order to be visible from the interior surface, the active graphics may be applied to a liquid permeable bodyside liner, to a surge layer, to a portion of the absorbent core, or even to the outer cover material in certain embodiments. When applied to the interior surface of an article, the active graphics need not be surrounded or associated with a framing device, outline, silhouette, or the like.

Referring to FIG. 3, absorbent articles generally include an outer cover 12 that includes an exterior surface and an interior surface. Located adjacent the interior surface is an absorbent structure 15. Optionally, the absorbent article can also include a liquid permeable inner lining 14. The absorbent structure can be placed in between the outer cover 12 and the inner lining 14. The absorbent article 10 can further include elastic waistbands 16 and 18 and elastic leg members 20 and 22.

The absorbent article 10 as shown in FIG. 1 can be made from various materials. The outer cover 12 may be made from a material that is substantially liquid impermeable, and can be elastic, stretchable or nonstretchable. The outer cover 12 can be a single layer of liquid impermeable material, or may include a multi-layered laminate structure in which at least one of the layers is liquid impermeable. For instance, the outer cover 12 can include a liquid permeable outer layer and a liquid impermeable inner layer that are suitably joined together by a laminate adhesive.

For example, in one embodiment, the liquid permeable outer layer may be a spunbond polypropylene nonwoven web. The spunbond web may have, for instance, a basis weight of from about 15 gsm to about 25 gsm.

The inner layer, on the other hand, can be both liquid and vapor impermeable, or can be liquid impermeable and vapor permeable. The inner layer is suitably manufactured from a thin plastic film, although other flexible liquid impermeable materials may also be used. The inner layer prevents waste material from wetting articles such as bedsheets and clothing, as well as the wearer and caregiver. A suitable liquid impermeable film may be a polyethylene film having a thickness of about 0.2 mm.

A suitable breathable material that may be used as the inner layer is a microporous polymer film or a nonwoven fabric that has been coated or otherwise treated to impart a desired level of liquid impermeability. Other "non-breathable" elastic films that may be used as the inner layer include films made from block copolymers, such as styrene-ethylene-butylene-styrene or styrene-isoprene-styrene block copolymers.

As described above, the absorbent structure is positioned in between the outer cover and a liquid permeable bodyside liner 14. The bodyside liner 14 is suitably compliant, soft feeling, and non-irritating to the wearer's skin. The bodyside liner 14 can be manufactured from a wide variety of web materials, such as synthetic fibers, natural fibers, a combination of natural and synthetic fibers, porous foams, reticulated foams, apertured plastic films, or the like. Various woven and non-woven fabrics can be used for the bodyside liner 14. For example, the bodyside liner can be made from a meltblown or spunbonded web of polyolefin fibers. The bodyside liner can also be a bonded-carded web composed of natural and/or synthetic fibers.

A suitable liquid permeable bodyside liner 14 is a non-woven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber. In this particular embodiment, the polypropylene forms the core and the polyethylene forms the sheath of the fiber. Other fiber orientations, however, are possible.

The material used to form the absorbent structure, for example, may include cellulosic fibers (e.g., wood pulp fibers), other natural fibers, synthetic fibers, woven or non-woven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent web material is a matrix of cellulosic fluff and superabsorbent hydrogel-forming particles. The cellulosic fluff may comprise a blend of wood pulp fluff. One preferred type of fluff is identified with the trade designation CR 1654, available from US Alliance Pulp Mills of Coosa, Ala., USA, and is a bleached, highly absorbent wood pulp containing primarily soft wood fibers. As a general rule, the superabsorbent material is present in the absorbent web in an amount of from about 0 to about 90 weight percent based on total weight of the web. The web may have a density within the range of about 0.1 to about 0.45 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 15 times its weight in liquid, and suitably is capable of absorbing more than about 25 times its weight in liquid. Suitable superabsorbent materials are readily available from various suppliers. For example, FAVOR® SXM 880 polyacrylate superabsorbent is available from Stockhausen, Inc., of Greensboro, N.C., USA; and DRYTECH® 2035 polyacrylate superabsorbent is available from Dow Chemical Company, of Midland, Mich., USA.

In addition to cellulosic fibers and superabsorbent materials, the absorbent pad structures may also contain adhesive elements and/or synthetic fibers that provide stabilization and attachment when appropriately activated. Additives such as adhesives may be of the same or different aspect from the cellulosic fibers; for example, such additives may be fibrous, particulate, or in liquid form; adhesives may possess either a curable or a heat-set property. Such additives can enhance the integrity of the bulk absorbent structure, and alternatively or additionally may provide adherence between facing layers of the folded structure.

The absorbent materials may be formed into a web structure by employing various conventional methods and techniques. For example, the absorbent web may be formed with a dry-forming technique, an airlaying technique, a carding technique, a meltblown or spunbond technique, a wet-forming technique, a foam-forming technique, or the like, as well as combinations thereof. Layered and/or laminated structures may also be suitable. Methods and apparatus for carrying out such techniques are well known in the art.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles or fibers, inorganic absorbent materials, treated polymeric staple fibers and the like. Any of a variety of synthetic polymers may be utilized as the melt-spun component of the coform material. For instance, in some embodiments, thermoplastic polymers can be utilized. Some examples of suitable thermoplastics that can be utilized include polyolefins, such as polyethylene, polypropylene, polybutylene and the like; polyamides; and polyesters. In one embodiment, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference for all purposes.

It is also contemplated that elastomeric absorbent web structures may be used. For example, an elastomeric coform absorbent structure having from about 35% to about 65% by weight of a wettable staple fiber, and greater than about 35% to about 65% by weight of an elastomeric thermoplastic fiber may be used to define absorbent pad structures according to the invention. Examples of such elastomeric coform materials are provided in U.S. Pat. No. 5,645,542, incorporated herein in its entirety for all purposes. As another example, a suitable absorbent elastic nonwoven material may include a matrix of thermoplastic elastomeric nonwoven filaments present in an amount of about 3 to less than about 20% by weight of the material, with the matrix including a plurality of absorbent fibers and a super-absorbent material each constituting about 20-77% by weight of the material. U.S. Pat. No. 6,362,389 describes such a nonwoven material and is incorporated herein by reference in its entirety for all purposes. Absorbent elastic nonwoven materials are useful in a wide variety of personal care articles where softness and conformability, as well as absorbency and elasticity, are important.

The absorbent web may also be a nonwoven web comprising synthetic fibers. The web may include additional natural fibers and/or superabsorbent material. The web may have a density in the range of about 0.1 to about 0.45 grams per cubic centimeter. The absorbent web can alternatively be a foam.

As shown in FIGS. 1 and 2, the absorbent article 10 can include side panels 24 and 26. The side panels 24 and 26 can have a color that blends with the overall scene appearing on the absorbent article. The side panels 24 and 26 can be permanently bonded together or can be releasably attached to one another. In FIG. 3, for instance, the side panels 24 and 26 are shown in an unattached state. In general, the side panels 24 and 26 are made from an elastic material, such as an elastic laminate.

As shown particularly in FIG. 3, the absorbent article 10 defines a longitudinal center line 3, a transverse center line 32, a first or front longitudinal end edge 34, and a second or back longitudinal end edge 36. The longitudinal axis lies in the plane of the article and is generally parallel to a vertical plane that bisects a standing wearer into left and right body halves when the article is worn. The transverse axis lies in the plane of the article generally perpendicular to the longitudinal axis.

In general, the absorbent article along the longitudinal axis can be divided into a front region 40, a back region 44, and a crotch region 42 positioned in between the front region and the back region. In one embodiment, the front region, the crotch region, and the back region can all have approximately the same length in the longitudinal direction.

The absorbent article can also be divided into a front half and a back half. The front half, for instance, may extend in the longitudinal direction from the front edge to the midpoint of the product, while the back half may extend from the back edge to the midpoint of the product.

As shown in FIGS. 1 through 3, the absorbent article 10 includes wetness sensing graphics. In accordance with the present disclosure, the entire scene displayed on the outer cover of the absorbent article can be made from a combination of permanent graphics and active graphics. In the embodiment illustrated, for instance, the scene depicts two main car or vehicle characters 50 and 52. The car characters 50 and 52 appear on a background 54 with further graphics. The background 54, for instance, may provide further scene details. In the embodiment illustrated, for instance, the background 54 depicts a race track stadium. Alternatively, the background 54 may simply be a solid color that matches the color of the side panels 24 and 26 while contrasting against the car characters 50 and 52.

In the embodiment illustrated, the car characters 50 and 52 and the background 54 may all comprise permanent graphics.

In the foreground to the car characters 50 and 52 is a framing device 56 surrounding active graphics 58. The framing, device 56, in accordance with the present disclosure, is of a particular size and position so as to accentuate the active graphics 58. The framing device 56, for instance, may substantially surround the active graphics. For instance, the framing device may surround at least about 90% of the active graphics or may completely surround the active graphics as shown.

In one embodiment, the outer cover 12 defines a printable surface area that may be compared in relation to the size of the framing device and the amount of surface area occupied by the active and/or permanent graphics. It should be understood that the printed matter may cover more than the printable surface area of the outer cover depending upon the particular application. For instance, the outer cover may be wider in the waist region than the crotch region.

In one embodiment, the active graphics present within the framing device occupy greater than 1% of the printable surface area of the outer cover. For instance, the active graphics may occupy greater than 1.2% or greater than 1.4% of the printable surface area of the outer cover. The active graphics occupying the above proportions of the outer cover surface area is relatively large in comparison to many prior art products commercialized in the past.

In particular, the total surface area occupied by the active graphics within the framing device 56 may be greater than 800 mm$^2$, such as greater than 900 mm$^2$, such as greater than 1000 mm$^2$, such as even greater than 1200 mm$^2$. When the active graphics are contained in a framing device, they may, in various embodiments, have a surface area of less than about 140,000 mm$^2$, such as less than about 45,000 mm$^2$, such as less than about 20,000 mm$^2$.

The framing device 56, in one embodiment, may depict an object, image or character that is further integrated into the overall scene and storyline presented by the absorbent article. In the embodiment illustrated, for instance, the framing device 56 represents a tire and can be multi-colored.

The framing device 56 can include an inner perimeter and an outer perimeter. In one embodiment, the framing device may have a relatively large size so as to make the framing device prominent on the absorbent article. In one embodiment, the surface area defined by the outer perimeter of the framing device may occupy at least about 5% of the printable surface area of the outer cover (greater than about 10% of the printable surface area of the front half of the outer cover), such as greater than about 7.5% of the printable surface area of the outer cover (such as greater than about 15% of the printable surface area of the front half of the outer cover), such as greater than about 10% of the printable surface area of the outer cover (such as greater than about 20% of the printable surface area of the front half of the outer cover).

As described above, within the framing device 56 and/or intersecting the framing device are one or more active graphics 58. The active graphics are created by applying an active graphic composition to the outer cover of the absorbent article. The active graphic composition undergoes a change when contacted with a body fluid, such as urine. In accordance with the present disclosure, the change is significantly more noticeable than many prior art constructions allowing the wearer or caregiver to instantly recognize that the absorbent article is in a wet condition.

In the embodiment illustrated in FIGS. 1 and 2, for instance, the active graphics 58 comprise a concentric ring and a circle that are intended to appear as a hubcap for the tire. In one embodiment, the active graphic fades, turns clear or disappears when wetted. For instance, as shown in FIG. 2, after the absorbent article 10 is wetted, the active graphics 58 disappear and leave white space within the framing device 56.

The active graphic composition used to produce the active graphics can comprise a composition that is water soluble and thus dissolves and disperses when wetted. Alternatively, the active graphic composition may be water insoluble and may undergo a color change when contacted with urine. For instance, the active graphic composition may go from a blue to a clear color. Alternatively, the active graphics 58 may undergo a change from one color to another color or from one shade of color to another shade.

In one embodiment, the active graphics 58 contained within the framing device 56 occupies a substantial portion of the surface area within the perimeter of the framing device. In this manner, a reduced amount of "white space" is left inside the framing device 56. Minimizing white space significantly improves the ability of the wearer or caregiver to notice a change in the graphics when wetted. For example, in one embodiment, the framing device 56 includes an outer perimeter and an inner perimeter that defines the surface area therein. The active graphics may occupy greater than about 35% of the surface area defined by the inner perimeter, such as greater than about 40% of the surface area defined by the inner perimeter, such as greater than about 50% of the surface area defined by the inner perimeter. In general, the active graphic can occupy 100% of the surface area defined by the inner perimeter or less than about 90% of the surface area defined by the inner perimeter, such as less than about 80% of the surface area defined by the inner perimeter, such as less than about 70% of the surface area defined by the inner perimeter.

Although minimizing white space may be desirable when the product is dry, in one embodiment, the active graphics turn the same color as the white space, turn clear, fade or turn white thus dramatically increasing the white space on the absorbent article when the active graphics are activated. Substantially increasing the white space becomes a noticeable change on the product. In one embodiment, for instance, the white space on the printable surface area of one side of the product increases by greater than about 15%, such as greater than about 20%, such as greater than about 40%, such as greater than about 50%, such as even greater than about 60%. In other embodiments, the active graphics may be configured to decrease the amount of white space when activated. For instance, the product may include active graphics that turn from the same color of the white space to a different color. In this embodiment, the white space on the printable surface area may decrease by greater than about 15%, such as greater than about 20%, such as greater than about 40%, such as greater than about 50%, such as even greater than about 60%.

The active graphics and permanent graphics used to form the scene as shown in FIGS. 1 and 2 can be applied to the absorbent article in different ways. In one embodiment, for instance, the outer cover 12 of the absorbent article includes multiple layers. The outer cover 12 may include, for instance, an inner water impermeable film and an outer water permeable layer that may comprise, for instance, a nonwoven layer. The inner film may be clear such that graphics printed on the inner film can be visible from the exterior surface of the outer cover. As can be appreciated, the active graphics should be applied to the absorbent article such that they contact any bodily fluids that may be absorbed by the article. In this regard, the active graphics may be printed on the interior surface of the outer cover such as on the inner surface of the inner film. The permanent graphics, however, can be printed on other layers of the outer cover. The permanent graphics, for instance, can be printed on the exterior surface of the outer cover, or can be printed on any of the interior layers either on the side facing the wearer or on the side opposite the wearer.

When the active graphics are to be visible from an interior side of the garment, the active graphics can be applied to a bodyside liner, a surge material, a wrap sheet that surrounds an absorbent structure, or may even be applied to the outer cover as long as the active graphics are visible from the interior.

When printing the graphics on the absorbent article, the active graphics should remain in alignment with the permanent graphics such that the overall scene is integrated. In one embodiment, in order to allow for greater variance in print pattern registration, at least a portion of the framing device 56 may overlap with at least a portion of the active graphics 58. For instance, the printed perimeter of the framing device can be smaller than the printed perimeter of the active graphics within the framing device.

Another consideration when designing a scene comprised of permanent graphics and active graphics as shown in FIGS. 1 and 2 is the location of the active graphics on the absorbent article. In one embodiment, for instance, the active graphics 58 and/or the framing device 56 are located primarily within the crotch region 42 of the absorbent article as particularly shown in FIG. 3. In one embodiment, for instance, all of the active graphics may be contained within the crotch region while a portion or all of the framing devices may also be located within the crotch region. Having the active graphics in the crotch region ensures contact with urine if the absorbent article is wetted. As shown in FIGS. 1 and 2, however, the active graphics should also extend from the center of the absorbent article such that they are visible when the article is being worn. In one embodiment, for instance, the active graphics can have a center that is a distance from the center of the absorbent article where the longitudinal and transverse axes meet. For instance, the active graphics can have a center that measures from about 6 to about 20 cm from the center of the absorbent article.

Figure 4:
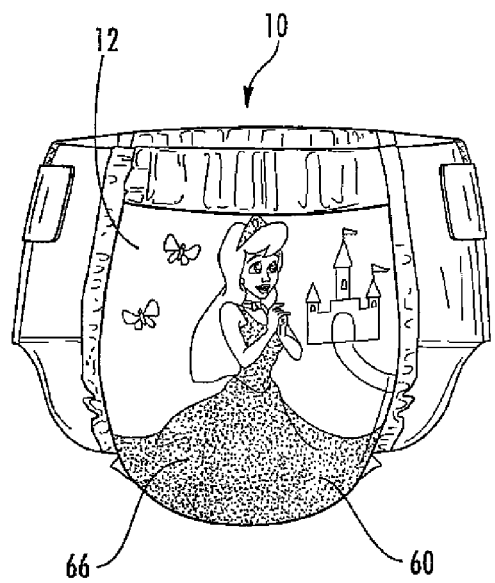
FIGS. 4 and 5 are plan views of an alternative embodiment of an absorbent article in accordance with the present disclosure including a wetness indicator.
Figure 5:
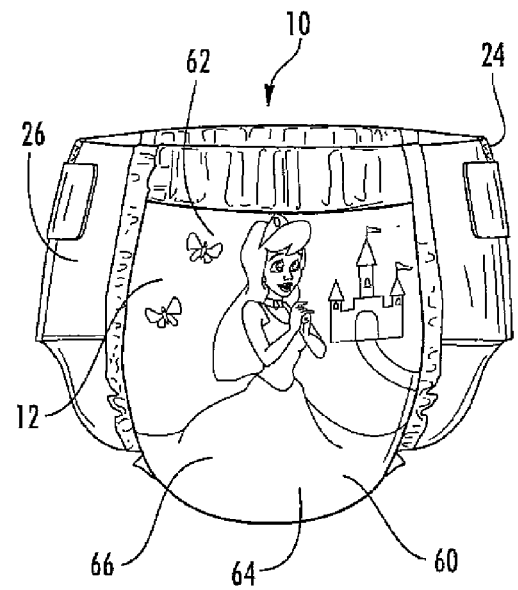

Referring to FIGS. 4 and 5, another embodiment of an absorbent article 10 made in accordance with the present disclosure is shown. Like reference numerals have been used to indicate similar elements: As shown, the absorbent article 10 includes an outer cover 12 and side panels 24 and 26 that form a chassis. In accordance with the present disclosure, a combination of permanent graphics and active graphics has been applied to the outer cover 12 in order to depict a scene. In this embodiment, the scene is intended to represent a princess 60 that is surrounded by a background 62. The background 62 includes solid colors and various images. The images include a castle, flowers and butterflies.

Instead of a framing device as shown in FIGS. 1 through 3, the embodiment illustrated in FIGS. 4 and 5 includes an outline 64 of the princess 60 that is comprised of permanent graphics. Active graphics 66 are located within and overlapping the outline 64. The active graphics, in this embodiment, are clothing items worn by the princess character including her dress and hair band.

The absorbent article 10 in FIG. 4 is shown in a dry state. FIG. 5, on the other hand, illustrates the absorbent article 10 once insulted with urine. As shown, the active graphics 56 are a color when the article is dry and turn clear or fade when the article is wetted.

As shown in FIGS. 4 and 5, the character princess takes up a substantial amount of the surface area of the outer cover 12. Further, the princess extends from the crotch region of the absorbent article into the front region of the absorbent article (or alternatively the back region of the absorbent article). Thus, the character princess and the outline 60 can occupy at least about 10%, such as at least about 20%, such as at least about 40%, such as at least about 60%, such as at least about 80% of the front half of the outer cover. In one embodiment, for instance, the character or active graphics can occupy 100% of the front half of the outer cover. In this manner, the surface area of the active graphics can be greater than 20,000 $mm^2$, such as greater than about 45,000 $mm^2$. The above provides for a very noticeable and prominent change in appearance when the absorbent article is wetted.

As described above, in the past, relatively small active graphics were printed on absorbent articles that were surrounded by significant amounts of white space. These active graphics faded when wetted by incorporating into the absorbent article water soluble inks. In one embodiment, however, by using a water insoluble composition that either changes from a first color to a second color or changes from a color to clear, much larger images can be applied to the absorbent article making the change in appearance much more dramatic when the article is wetted.

In the embodiment illustrated in FIGS. 4 and 5, the active graphic 66 goes from a color, such as blue, red, green, etc. to clear. In an alternative embodiment, however, the active graphic composition used to produce the active graphic may change from a first color or shade to a second color or shade.

In certain embodiments, the active graphic 66 may be also produced using water soluble inks. In this embodiment, the permanent graphics that form the outline 64 and the background 62 remain recognizable when the active graphics 64 disappears, fades or changes color.

The absorbent article illustrated in FIGS. 1 through 3 that includes car characters may be designed for use by boys, while the princess scene depicted in FIGS. 4 and 5 may be particularly well suited for girls. It should be understood, however, that the inventive concepts described in the embodiments can be used for either sex by designing the appropriate scene and using the appropriate colors.

In the embodiments illustrated in FIGS. 1 through 5, the scenes and active graphics present on the absorbent articles are particularly well suited for indicating that the absorbent article has been wetted. The wetness indicator can be used by adults or caregivers to prevent children from wearing wet diapers or can be used by children to assist in the toilet training process. When used as a toilet training tool, various other features can be incorporated into the active graphics for not only encouraging use of the toilet, but also for discouraging the wetting of the absorbent article. For instance, in one embodiment, the active graphics appearing in the scenes can undergo a color change when wetted. In particular, the active graphics can go from a pleasant color (e.g. blue or pink) to an undesirable color (e.g. pea green, gray, etc.).

Figure 11:
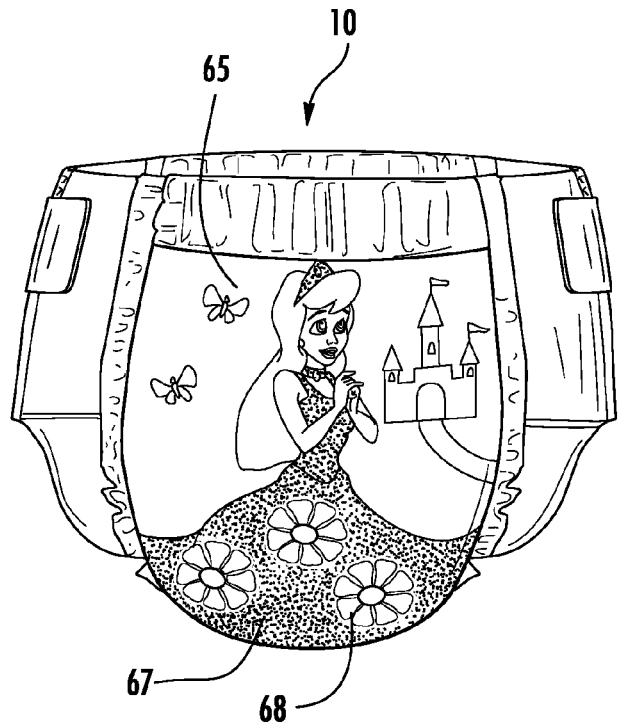
FIGS. 11 and 12 are plan views of an alternative embodiment of an absorbent article in accordance with the present disclosure including a wetness indicator.
Figure 12:
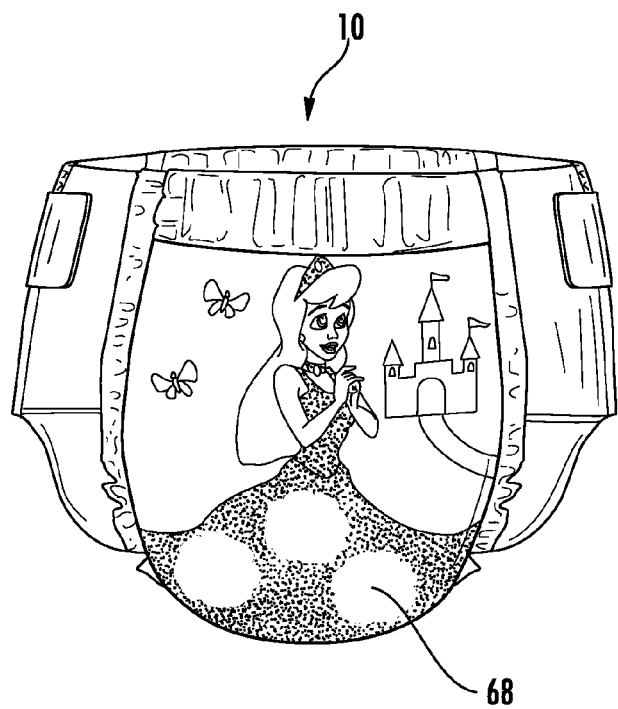

Referring to FIGS. 11 and 12, another embodiment of an absorbent article 10 similar to the article illustrated in FIGS. 4 and 5 is shown. In this embodiment, the outer cover 12 of the absorbent article depicts a character scene. The character scene includes a character surrounded by an integrated background 65 including various related objects and images. The character is comprised of permanent graphics and active graphics. The character 67 further forms a silhouette that surrounds, in this embodiment, flowers 68. Flowers 68 are comprised of an active graphic. As shown in FIG. 12, when the absorbent article is wetted, the flowers either change color or disappear.

Figure 6:
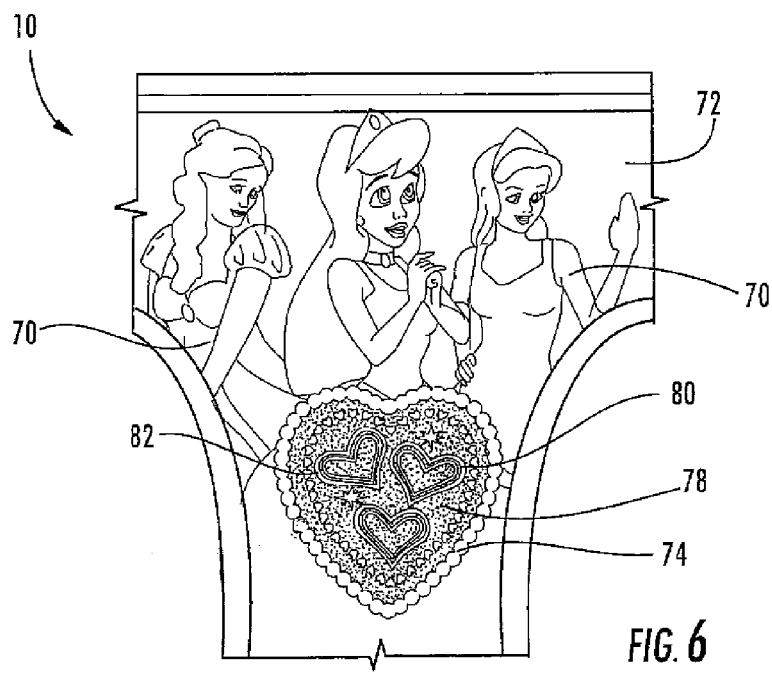
FIG. 6 is a partial view of another embodiment of an absorbent article made in accordance with the present disclosure including a wetness indicator.

Another embodiment of an absorbent article 10 made in accordance with the present disclosure is shown in FIG. 6. In FIG. 6, only the portion of the absorbent article is shown where the graphics are located. In accordance with the present disclosure, the scene depicted on the absorbent article 10 is made from a combination of permanent graphics and active graphics. The particular scene shown in FIG. 6 illustrates princess characters 70 appearing on a color background 72. The background color, for instance, may comprise any color that complements the appearance of the characters 70.

As shown, the scene further depicts a foreground graphic that includes a framing device 74, a background color 78, various heart-shaped outlines 80, and heart-shaped images 82. The foreground graphic serves as the wetness indicator for the entire scene. The various elements contained within the framing device 74 can be made from permanent graphics and active graphics. In one embodiment, for instance, only the heart-shaped images 82 are the active graphics. In an alternative embodiment, the heart-shaped graphics 82 and the background 78 comprise active graphics. In this manner, substantially all of the area within the framing device may turn to a different color or fade and disappear.

Figures 7, 8:
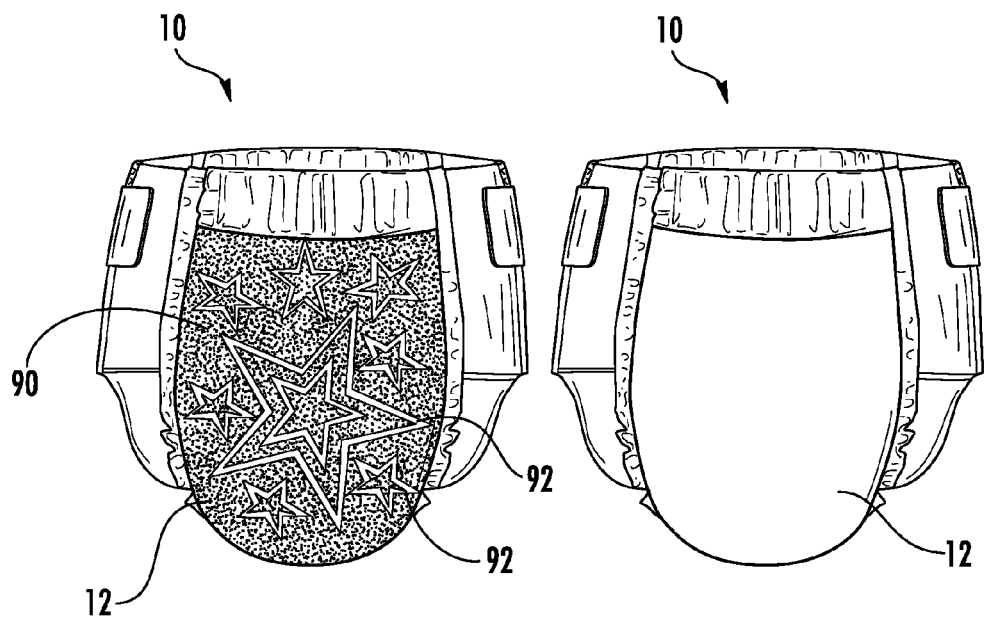
FIGS. 7 and 8 are plan views of an alternative embodiment of an absorbent article in accordance with the present disclosure including a wetness indicator.

Referring now to FIGS. 7 and 8, still another embodiment of an absorbent article 10 made in accordance with the present disclosure is shown. As illustrated, the absorbent article 10 includes an outer cover 12 that depicts a scene and is comprised of at least active graphics. More particularly, in this embodiment, the scene includes a background 90 comprised of active graphics that surround or cover other images. In the embodiment illustrated in FIG. 7, for instance, the background 90 comprised of active graphics, surrounds a plurality of stars 92. The stars 92 can be made in various ways. For example, in one embodiment, the stars 92 can be made from an active graphic composition or from a permanent graphic composition. Alternatively, the background 90 may be made from an active graphic composition that is applied to the outer cover in a manner that forms treated areas and untreated areas. The stars 92 may comprise the untreated areas.

FIG. 7 represents the absorbent article 10 in a dry state, while FIG. 8 illustrates the absorbent article once wetted. As shown, once wetted, the background 90 changes color or fades. In this manner, the entire scene disappears once the background 90 is contacted with urine. Of particular advantage, by having the background 90 comprise an active graphic that changes color, fades, disappears or appears, almost the entire surface of the outer cover 12 changes in appearance when the absorbent article is wetted. In this manner, the wetness indicator becomes clearly noticeable when a change occurs.

Figures 9, 10:
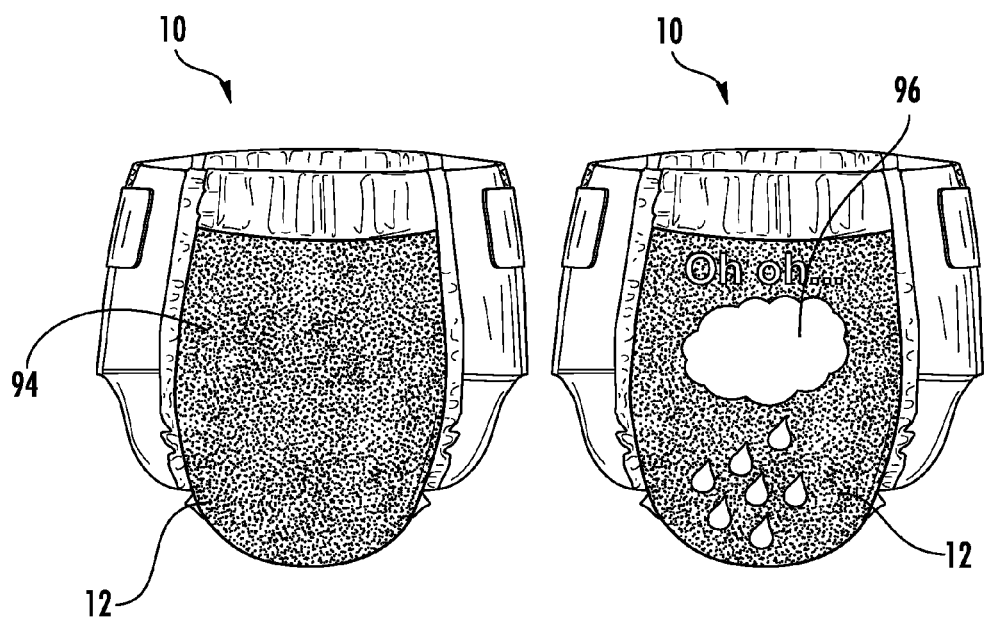
FIGS. 9 and 10 are plan views of an alternative embodiment of an absorbent article in accordance with the present disclosure including a wetness indicator.

Referring to FIGS. 9 and 10, another embodiment of an absorbent article 10 is shown. In this embodiment, the absorbent article 10 includes an outer cover 12 that depicts a scene comprised of permanent graphics and active graphics. As shown in FIG. 9, the absorbent article 10 includes a background color 94 and active graphics 96 that are not visible when the product is dry. More particularly, when the product is dry, the entire outer cover appears as a single color or shade. Once wetted, however, as shown in FIG. 10, the active graphics 96 become visible.

In one embodiment, for instance, the active graphics 96 may be comprised of an active graphic composition that changes from a first color to a second color (such as a shade change) or changes from a first color to clear. The first color can be substantially the same color as the background 94 which is comprised of a permanent graphic composition. In this manner, the active graphics 96 are not discernible on the product when it is dry but become readily noticeable when the absorbent article 10 has been wetted. As shown in FIG. 10, in one embodiment, the active graphics 96 may comprise words, phrases, and various images. In other embodiments, however, a complete colorized scene may appear including characters and objects.

In an alternative embodiment, the background 94 may be comprised of an active graphic, while the image or scene that appears once the article is wetted may be comprised of a permanent graphic 96. In this embodiment, instead of the image changing color or turning to clear, the background 94 may change color or turn clear thus making the image 96 visible.

Figure 13:
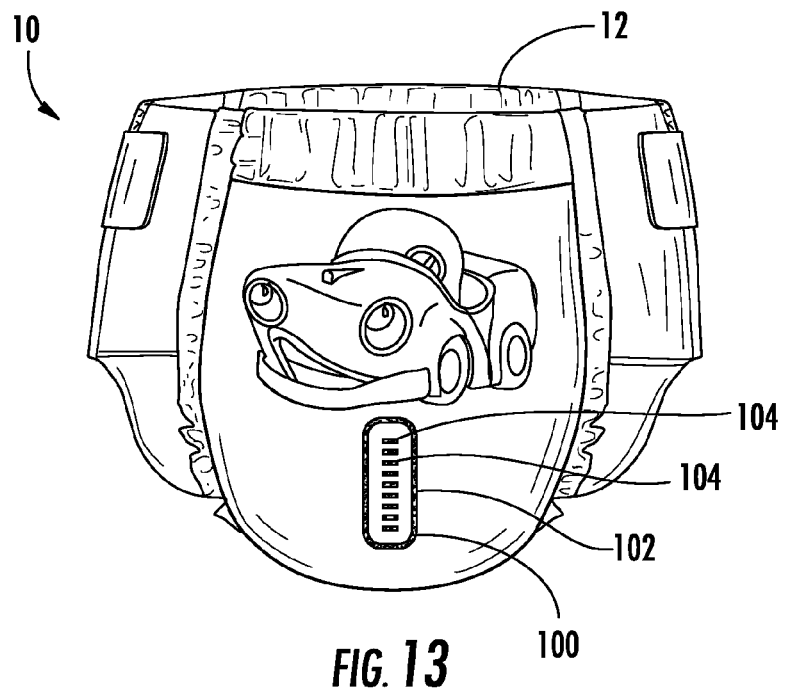
FIG. 13 is a perspective view of another alternative embodiment of an absorbent article in accordance with the present disclosure including a wetness indicator.

Referring to FIG. 13, still another embodiment of an absorbent article 10 made in accordance with the present disclosure is shown. In the embodiment illustrated in FIG. 13, the absorbent article includes an outer cover 12 that depicts a scene. The scene may comprise, for instance, a character with background and foreground graphics. The scene depicted upon the absorbent article 10 may be comprised entirely of permanent graphics.

In accordance with the present disclosure, the absorbent article 10 as shown in FIG. 13 further includes a wetness indicator 100 that is designed to undergo a change when contacted with a body exudate. As shown, the wetness indicator 100 comprises a gauge-like graphic. In this embodiment as opposed to the other embodiments illustrated above, the wetness indicator 100 is relatively small and is not integrated or in any way tied to the overall scene displayed on the garment. Instead, the wetness indicator 100 is visually different from the other graphics on the outer cover and appears to have a more functional appearance. In this manner, the wetness indicator 100 is visually distinct on the outer cover.

Although visually distinct, because the wetness indicator 100 is relatively small, the wetness indicator may also provide some discretion to the wearer of the absorbent article. For example, although the gauge-like graphic is easy to recognize, the size of the graphic can be such that it would not be readily noticeable to a bystander.

As shown, the wetness indicator 100 includes a framing device 102 that includes an inner perimeter and an outer perimeter. Within the inner perimeter of the framing device 102 are gauge elements 104, which comprise a column of spaced apart bars. The gauge elements 104 may be contained completely within the inner perimeter of the framing device 102 or may overlap with the framing device. The gauge elements may or may not be surrounded by a background color. The gauge elements 104 comprise active graphics that change color, such as change shade, or disappear when contacted with a liquid, such as urine. In one embodiment, for instance, the gauge elements may turn from color to clear when contacted with a body fluid. The framing device 102 focuses one's attention on the gauge elements for better discerning when the wetness indicator has been wetted.

As described above, in the embodiment in FIG. 13, the wetness indicator 100 can be relatively small in relation to the overall surface area of the outer cover. For instance, the active graphics contained within the wetness indicator 100 may have a surface area of less than about 150 mm$^2$, such as less than about 120 mm$^2$, such as less than about 90 mm$^2$. The active graphics may have a surface area of generally greater than about 20 mm$^2$, such as greater than about 50 mm$^2$, such as greater than about 70 mm$^2$.

As defined above, the outer cover 12 includes a printable surface area. The active graphics or gauge elements 104 may occupy generally less than about 1% of the printable surface area of the outer cover, such as less than about 0.2% of the printable surface area of the outer cover, such as less than about 0.15% of the printable surface area, such as less than about 0.12% of the printable surface area.

With respect to the surface area defined by the inner perimeter of the framing device 102, the active graphics occupy generally less than about 30% of the surface area, such as less than about 20% of the surface area, such as less than about 15% of the surface area, especially when a background color is not present. If a background color is present, the active graphics can occupy greater than about 70%, such as greater than about 80%, such as greater than about 90% of the inner surface area (up to 100% of the surface area).

In the embodiment illustrated in FIG. 13, the gauge elements 104 are formed by the active graphics and are surrounded by white space or a background color within the framing device 1 or 2. In an alternative embodiment, the wetness indicator 100 may comprise a background color within the framing device 102. The gauge elements 104 may be formed where the background color has not been applied to the surface of the absorbent article.

Figure 14:
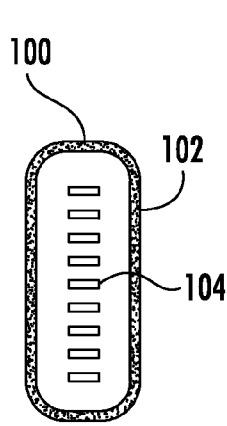
FIGS. 14 through 19 are plan views of other embodiments of wetness indicators.
Figure 15:
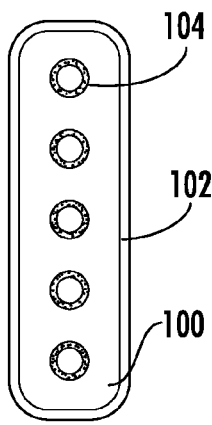
Figure 16:
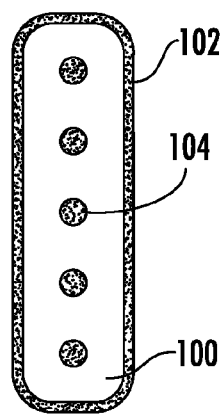
Figure 17:
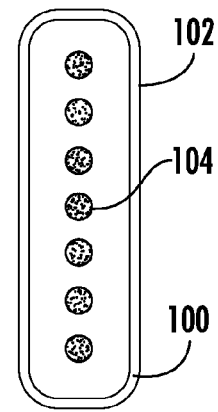
Figure 19:
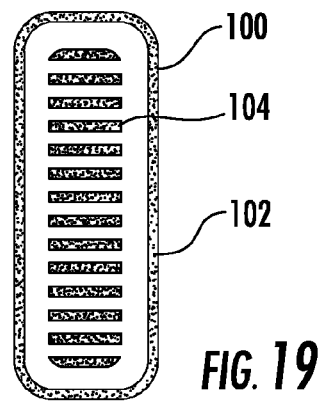

Referring to FIGS. 14 through 17 and 19, various other wetness indicators 100 similar to the one illustrated in FIG. 13 are shown. In FIGS. 14 and 19, the gauge elements generally comprise a column of bars contained within a framing device 102. In FIGS. 15 through 17, on the other hand, the gauge elements comprise a column of dots 104 contained within the framing device 102.

Figure 18:
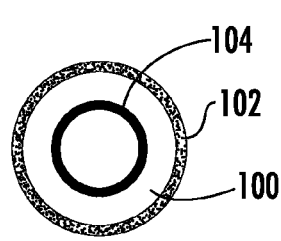

Referring to FIG. 18, still another embodiment of a wetness indicator 100 is shown that includes a circular framing device 102 that encloses a gauge element 104 comprised of active graphics. In this embodiment, only a single gauge element is present in the framing device. The gauge element is circular and concentric with the framing device. The gauge element 104 may comprise a solid circle as shown or may have a ring-like shape that includes white space or a background color in the center.

In the above examples, the active and permanent graphics were applied to the exterior surface of an absorbent article. It should be understood, however, that the above graphics can be applied equally so as to be visible from the interior surface of an absorbent article. In one embodiment, for instance, active graphics may be applied to both the exterior surface and to the interior surface of the absorbent article. When applied to the interior surface of the absorbent article, a gauge-like graphic may be used as shown in FIG. 13. Alternatively, a relatively large active graphic may be applied to the interior surface. The active graphic, for instance, may have a surface area of greater than about 800 mm$^2$ or may have any of the dimensions described above depending upon the particular type of product. For example, in one embodiment, the active graphic can be visible from the interior surface of the absorbent article and have a size such that the active graphic(s) occupies greater than about 1% of the printable surface area of the interior surface.

Various aspects of the present disclosure may be better understood with reference to the following example.

EXAMPLE

In the following example, 18 absorbent articles sold in the past that contained graphic wetness indicators were analyzed in relation to 6 absorbent articles in accordance with the present disclosure. Sample Nos. 1 and 2 in accordance with the present disclosure were similar to the design illustrated in FIG. 4. Sample No. 3 in accordance with the present disclosure, on the other hand, was similar in design to FIGS. 1 through 3. Sample Nos. 4 and 5 were similar in design to the embodiment illustrated in FIG. 6. Sample No. 6 included a gauge-like design as illustrated in FIG. 13.

As shown in the tables below, various characteristics of the graphics applied to the absorbent articles were measured including the printable surface area of the outer cover, the surface area of the active graphics, and the ratio of the above two measurements. In addition, inner and outer perimeters of various graphics were measured. It should be understood, however, that Applicants do not in any way admit that any of the comparative samples contained a framing device or outline as those terms are used in the present application.

The data in the Table below was generated by manipulating images of a product or product drawing in an open and laid flat configuration. Graphics within image files were converted to 100% black. Images were then imported to PHOTOSHOP software in grayscale format. A product called Image Analysis Toolkit from Reindeer Graphics was used as an Add-in with PHOTOSHOP software to calculate the black area of the image and provided as a percentage of the selected image area defined by the Width and Height. The Border thickness of the frame and largest dimension of the frame were determined manually with a ruler. Other values in the table were calculated. The following are definitions of the terms used in the table.

% Inner Perimeter Surface Area in Relation to Printable Surface Area: Area defined by the inner perimeter of the framing device or outline with respect to the total area of the image defined by the width and height.

% Outer Perimeter Surface Area in Relation to Printable Surface Area: Area defined by the outer perimeter of the framing device or the outline or the silhouette with respect to the total area of the image defined by the width and height.

% Active Graphics Surface Area: Area defined by the actual area of the active graphic, not including any background that may be within the perimeter of the active graphic that does not change color when wetted with respect to the total area of the image defined by the width and height.

% Active Graphics Perimeter Surface Area: Area defined by the perimeter of the outermost elements of the active graphic with respect to the total area of the image defined by the width and height.

For example in a line drawing of a flower, the outside border of the flower defines the area to be calculated. If multiple elements make up the active graphic, such as in the gauge with multiple elements (FIG. 14), the individual elements are added together to determine the area.

% White Area: Area of white with respect to the total area of the image defined by the width and height.

Border Thickness: Widest dimension of a border between inner and outer perimeter.

Largest Dimension of Framing Device or Outline: Longest linear dimension between two points on the outer perimeter.

Printable Surface Area: Area defined by width and height of image.

Inner Perimeter Area (mm2): Actual area defined by the inner perimeter calculated from % Inner Perimeter Surface Area and Printable Surface Area.

Outer Perimeter Area (mm2): Actual area defined by the outer perimeter calculated from % Outer Perimeter Surface Area and Printable Surface Area Area of Framing Device or Border (mm2): Outer Perimeter Area minus Inner Perimeter Area. Area of framing device between the outer and inner perimeter.

Active Graphics Surface Area (mm2): Actual area defined by the active graphic, not including any background that may be within the perimeter of the active graphic that does not change color when wetted. Calculated from % Active Graphic Surface Area and Printable Surface Area.

Active Graphics Perimeter Surface Area (mm2): Actual area defined by the perimeter of the outermost elements of the active graphic with respect to the total area of the image defined by the width and height. Calculated from % Active Graphic Perimeter Surface Area and Printable Surface Area.

Initial White Space Area (mm2): Actual white area of possible printed area. White can be from a non printed area over a white substrate or can be a printed or otherwise white colored area. Calculated from % White Area and Printable Surface Area White Space Area Once Active Graphics Activated (mm2): Actual white area of Printable Surface Area plus area of active graphic that changes to white. The active graphic can change to a white color or can disappear from a white background.

% Increase in White space: Percentage of increase of white space area as a result of an active graphic disappearing to a white background or changing to a white color.

The following results were obtained.

| Sample No. | Width (mm) | Height (mm) | Front Only Height (mm) | Printable Surface Area on Outer Cover (sqmm) - Calculated | Printable Surface Area on Front Half of Outer Cover (sqmm) - Calculated | % Inner Perimeter Surface Area in Relation to Printable Surface Area | % Inner Perimeter Surface Area in Relation to Printable Surface Area of Front Half of Outer Cover | % Outer Perimeter Surface Area in Relation to Printable Surface Area | % Outer Perimeter Surface Area in Relation to Printable Surface Area of Front Half of Outer Cover | % Active Graphics Coverage in Relation to Printable Surface Area | % Active Graphics Coverage Based on Front Half of Outer Cover in Relation to Printable Surface Area | % Active Graphic Perimeter Surface Area in Relation to Printable Surface Area | % Active Graphic Perimeter Surface Area in Relation to Printable Surface Area Based on Front Half of Outer Cover | % White Area of Product Graphics | Border Thickness (mm) - Manual |
|---|---|---|---|---|---|---|---|---|---|---|---|---|---|---|---|
| Comparative Sample No. 1 | 169 | 461 | 230.5 | 77909 | 38955 | 4.15 | 8.30 | 4.15 | 8.30 | 0.36 | 0.72 | 0.52 | 1.04 | 15.41 | 0 |
| Comparative Sample No. 2 | 169 | 461 | 230.5 | 77909 | 38955 | 3.44 | 6.88 | 3.83 | 7.66 | 0.36 | 0.72 | 0.52 | 1.04 | 14.81 | 0 |
| Comparative Sample No. 3 | 169 | 461 | 230.5 | 77909 | 38955 | 2.87 | 5.74 | 2.87 | 5.74 | 0.29 | 0.58 | 0.39 | 0.78 | 14.24 | 0 |
| Comparative Sample No. 4 | 169 | 450.85 | 225.4 | 76194 | 38097 | 4.39 | 8.78 | 4.39 | 8.78 | 0.37 | 0.74 | 0.56 | 1.12 | 15.60 | 0 |
| Comparative Sample No. 5 | 169 | 450.85 | 225.4 | 76194 | 38097 | 2.78 | 5.56 | 3.45 | 6.90 | 0.34 | 0.68 | 0.69 | 1.38 | 14.67 | 3.5 |
| Comparative Sample No. 6 | 169 | 450.85 | 225.4 | 76194 | 38097 | 4.49 | 8.98 | 4.97 | 9.94 | 0.37 | 0.74 | 0.56 | 1.12 | 6.92 | 0 |
| Comparative Sample No. 7 | 169 | 450.85 | 225.4 | 76194 | 38097 | 3.06 | 6.12 | 3.99 | 7.98 | 0.36 | 0.72 | 0.62 | 1.24 | 4.15 | 2 |
| Comparative Sample No. 8 | 169 | 450.85 | 225.4 | 76194 | 38097 | 3.08 | 6.16 | 3.38 | 6.76 | 0.34 | 0.68 | 0.69 | 1.38 | 5.94 | 0 |
| Comparative Sample No. 9 | 169 | 450.85 | 225.4 | 76194 | 38097 | 1.69 | 3.38 | 2.05 | 4.10 | 0.50 | 1.00 | 0.61 | 1.22 | 29.53 | 2 |
| Comparative Sample No. 10 | 169 | 525 | 262.5 | | | 2.51 | 5.02 | 2.51 | 5.02 | 0.29 | 0.58 | NA | NA | 41.93 | 0 |
| Comparative Sample No. 11 | 169 | 450.85 | 225.4 | 76194 | 38097 | 2.74 | 5.48 | 3.00 | 6.00 | 0.80 | 1.60 | 1.28 | 2.56 | 5.39 | 0.5 |
| Comparative Sample No. 12 | 169 | 450.85 | 225.4 | 76194 | 38097 | 3.06 | 6.12 | 3.60 | 7.20 | 0.94 | 1.88 | 1.58 | 3.16 | 11.42 | 1 |
| Comparative Sample No. 13 | 169 | 450.85 | 225.4 | 76194 | 38097 | 2.70 | 5.40 | 3.76 | 7.52 | 0.37 | 0.74 | 0.79 | 1.58 | 13.85 | 2 |
| Comparative Sample No. 14 | 169 | 450.85 | 225.4 | 76194 | 38097 | 3.79 | 7.58 | 4.39 | 8.78 | 0.28 | 0.56 | 1.09 | 2.18 | 7.84 | 0.5 |
| Comparative Sample No. 15 | 169 | 450.85 | 225.4 | 76194 | 38097 | 3.22 | 6.44 | 3.99 | 7.98 | 0.23 | 0.46 | 0.73 | 1.46 | 8.04 | 2.5 |
| Comparative Sample No. 16 | 169 | 450.85 | 225.4 | 76194 | 38097 | 1.57 | 3.14 | 2.22 | 4.44 | 0.36 | 0.72 | 0.58 | 1.16 | 8.70 | 2 |
| Comparative Sample No. 17 | 169 | 525 | 262.5 | | | 1.99 | 3.98 | 2.92 | 5.84 | 0.28 | 0.56 | 0.43 | 0.86 | 8.24 | 2 |
| Comparative Sample No. 18 | 169 | 525 | 262.5 | | | 2.09 | 4.18 | 2.83 | 5.66 | 0.56 | 1.12 | 0.80 | 1.60 | 12.68 | 1 |
| Sample No. 1 | 169 | 501.65 | 250.8 | | | 3.81 | 7.62 | 4.83 | 9.66 | 2.99 | 5.98 | 3.58 | 7.16 | 5.36 | 0.5 |
| Sample No. 2 | 169 | 501.65 | 250.8 | | | 9.59 | 19.18 | 11.16 | 22.32 | 9.29 | 18.58 | 9.31 | 18.62 | 13.30 | 0.5 |
| Sample No. 3 | 169 | 430 | 215.0 | | | 4.52 | 9.04 | 8.33 | 16.66 | 1.40 | 2.80 | 2.12 | 4.24 | 21.15 | 5 |
| Sample No. 4 | 169 | 430 | 215.0 | | | 4.69 | 9.38 | 5.71 | 11.42 | 1.41 | 2.82 | 2.29 | 4.58 | 14.09 | 3 |
| Sample No. 5 | 169 | 451 | 225.5 | | | 4.65 | 9.30 | 5.46 | 10.92 | 2.96 | 5.92 | 3.18 | 6.36 | 13.26 | 2 |
| Sample No. 6 | 169 | 430 | 215.0 | | | 0.74 | 1.48 | 1.02 | 2.04 | 0.11 | 0.22 | 0.20 | 0.40 | 45.96 | 1 |

| Sample No. | Largest Dimension of Framing Device or Outline (mm) - Manual | Inner Perimeter Area (sqmm) | Outer Perimeter Area (sqmm) | Area of Framing Device or Border (sqmm) | Active Graphics Surface Area (sqmm) | Active Graphics Perimeter Surface Area (sqmm) | % Active Graphic Surface Area of Inner Perimeter Surface Area | % Active Graphics Perimeter Surface Area of Inner Perimeter Surface Area | Ratio of Active Graphics Surface Area to Active Graphics Perimeter Surface Area | Initial White Space Area (sqmm) | White Space Area Once Active Graphics Activate | % Increase in White Space Once Active Graphics Activate |
|---|---|---|---|---|---|---|---|---|---|---|---|---|
| Comparative Sample No. 1 | 56 | 3233 | 3233 | 0 | 280 | 405 | 8.67 | 12.53 | 0.69 | 12006 | 12286 | 2.34 |
| Comparative Sample No. 2 | 62 | 2680 | 2984 | 304 | 280 | 405 | 10.47 | 15.12 | 0.69 | 11538 | 11819 | 2.43 |
| Comparative Sample No. 3 | 81 | 2236 | 2236 | 0 | 226 | 304 | 10.10 | 13.59 | 0.74 | 11094 | 11320 | 2.04 |
| Comparative Sample No. 4 | 97 | 3345 | 3345 | 0 | 282 | 427 | 8.43 | 12.76 | 0.66 | 11886 | 12168 | 2.37 |
| Comparative Sample No. 5 | 70 | 2118 | 2629 | 510 | 259 | 526 | 12.23 | 24.82 | 0.49 | 11178 | 11437 | 2.32 |
| Comparative Sample No. 6 | 95 | 3421 | 3787 | 366 | 282 | 427 | 8.24 | 12.47 | 0.66 | 5273 | 5555 | 5.35 |
| Comparative Sample No. 7 | 60 | 2332 | 3040 | 709 | 274 | 472 | 11.76 | 20.26 | 0.58 | 3162 | 3436 | 8.67 |
| Comparative Sample No. 8 | 62 | 2347 | 2575 | 229 | 259 | 526 | 11.04 | 22.40 | 0.49 | 4526 | 4785 | 5.72 |
| Comparative Sample No. 9 | 40 | 1288 | 1562 | 274 | 381 | 465 | 29.59 | 36.09 | 0.82 | 22500 | 22881 | 1.69 |

-continued

| Sample | | | | | | | | | | | | | | |
|---|---|---|---|---|---|---|---|---|---|---|---|---|---|---|
| Comparative Sample No. 10 | 90 | 88725 | 44363 | 2227 | 2227 | 0 | 257 | NA | 11.55 | NA | NA | 37202 | 37460 | 0.69 |
| Comparative Sample No. 11 | 50 | 76194 | 38097 | 2088 | 2286 | 198 | 610 | 975 | 29.20 | 46.72 | 0.63 | 4107 | 4716 | 14.84 |
| Comparative Sample No. 12 | 57 | 76194 | 38097 | 2332 | 2743 | 411 | 716 | 1204 | 30.72 | 51.63 | 0.59 | 8701 | 9418 | 8.23 |
| Comparative Sample No. 13 | 60 | 76194 | 38097 | 2057 | 2865 | 808 | 282 | 602 | 13.70 | 29.26 | 0.47 | 10553 | 10835 | 2.67 |
| Comparative Sample No. 14 | 87 | 76194 | 38097 | 2888 | 3345 | 457 | 213 | 831 | 7.39 | 28.76 | 0.26 | 5974 | 6187 | 3.57 |
| Comparative Sample No. 15 | 68 | 76194 | 38097 | 2453 | 3040 | 587 | 175 | 556 | 7.14 | 22.67 | 0.32 | 6126 | 6301 | 2.86 |
| Comparative Sample No. 16 | 44 | 76194 | 38097 | 1196 | 1691 | 495 | 274 | 442 | 22.93 | 36.94 | 0.62 | 6629 | 6903 | 4.14 |
| Comparative Sample No. 17 | 50 | 88725 | 44363 | 1766 | 2591 | 825 | 248 | 382 | 14.07 | 21.61 | 0.65 | 7311 | 7559 | 3.40 |
| Comparative Sample No. 18 | 31 | 88725 | 44363 | 1854 | 2511 | 657 | 497 | 710 | 26.79 | 38.28 | 0.70 | 11250 | 11747 | 4.42 |
| Sample No. 1 | 98 | 84779 | 42389 | 3230 | 4095 | 865 | 2535 | 3035 | 78.48 | 93.96 | 0.84 | 4544 | 7079 | 55.78 |
| Sample No. 2 | 159 | 84779 | 42389 | 8130 | 9461 | 1331 | 7876 | 7893 | 96.87 | 97.08 | 1.00 | 11276 | 19152 | 69.85 |
| Sample No. 3 | 88 | 72670 | 36335 | 3285 | 6053 | 2769 | 1017 | 1541 | 30.97 | 46.90 | 0.66 | 15370 | 16387 | 6.62 |
| Sample No. 4 | 42 | 72670 | 36335 | 3408 | 4149 | 741 | 1025 | 1664 | 30.06 | 48.83 | 0.62 | 10239 | 11264 | 10.01 |
| Sample No. 5 | 78 | 76219 | 38110 | 3544 | 4162 | 617 | 2256 | 2424 | 63.66 | 68.39 | 0.93 | 10107 | 12363 | 22.32 |
| Sample No. 6 | 20 | 72670 | 36335 | 538 | 741 | 203 | 80 | 145 | 14.86 | 27.03 | 0.55 | 33399 | 33479 | 0.24 |

As shown above, the surface area of active graphics used in conjunction with some embodiments of the present disclosure are much larger than the previous commercial products. In addition, the active graphics of Samples 1 and 2 in accordance with the present disclosure occupied a significantly greater amount of the surface area of the printable surface area of the outer cover.

Sample No. 3 in accordance with the present disclosure which included a wetness indicator having a gauge-like appearance occupied a much smaller amount of space than many prior products, while still remaining visibly distinct.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An absorbent article comprising:
    an outer cover having an interior surface and an exterior surface, wherein the outer cover includes an initial amount of white space;
    an absorbent structure positioned adjacent to the interior surface of the outer cover;
    at least one active graphic incorporated into the absorbent article such that the at least one active graphic is visible from a surface of the article; and
    a framing device or an outline that substantially surrounds the at least one active graphic, wherein the framing device or the outline is concentric with the at least one active graphic and highlights the at least one active graphic, the framing device or outline comprising a permanent graphic and all of the active graphics having a total surface area of at least 800 mm$^2$, wherein the framing device or the outline has a perimeter that defines a surface area therein, all of the active graphics present occupying from about 35% to about 90% of the surface area of the framing device or outline, wherein once the active graphics are activated, the amount of white space on the outer cover changes at least by 15%.

2. An absorbent article as defined in claim 1, wherein the absorbent article includes a front region, a back region, and a crotch region positioned in between the front region and the back region, wherein more than 50% of the framing device or outline is located in the crotch region.

3. An absorbent article as defined in claim 1, wherein the framing device surrounds multiple active graphics.

4. An absorbent article as defined in claim 1, wherein the at least one active graphic is formed by applying an active graphic composition onto the outer cover of the absorbent article, the outer cover having a printable surface area, all of the active graphics present occupying at least 1% of the printable surface area of the outer cover.

5. An absorbent article as defined in claim 4, wherein all of the active graphics present have a total surface area of at least 1000 mm$^2$.

6. An absorbent article as defined in claim 1, wherein at least a portion of the framing device overlaps a portion of the at least one active graphic.

7. An absorbent article as defined in claim 1, wherein the framing device comprises an object, image or character.

8. An absorbent article as defined in claim 1, wherein the at least one active graphic is disposed on the interior surface of the outer cover and the framing device is disposed on the exterior surface of the outer cover.

9. An absorbent article as defined in claim 1, wherein the outer cover comprises a liquid permeable outer layer and a liquid impermeable inner layer, the at least one active graphic being disposed on the surface of the inner layer that forms the interior surface of the outer cover, the framing device or outline being disposed on an opposite surface of the inner layer.

10. An absorbent article as defined in claim 1, wherein the absorbent article includes a front region, a back region, and a crotch region positioned in between the front region and the back region, wherein more than 50% of the framing device or outline is located in the front region.

11. An absorbent article as defined in claim 1, wherein the outer cover of the absorbent article defines an exterior side and is opposite to an interior side of the absorbent article, the framing device and the at least one active graphic being visible from the exterior side of the absorbent article, the absorbent article further including at least one other active graphic that is visible from the interior side, the interior side having a printable surface area and all of the active graphics visible from the interior side occupying at least 1% of the printable surface area of the interior side.

12. An absorbent article comprising:
    an outer cover having an interior surface and an exterior surface;
    an absorbent structure positioned adjacent to the interior surface of the outer cover;
    at least one active graphic incorporated into the absorbent article;
    a framing device or an outline that substantially surrounds the active graphic, wherein the framing device or the outline is concentric with the at least one active graphic and highlights the at least one active graphic, the framing device or the outline comprising a permanent graphic and all of the active graphics having a total surface area of at least 800 mm$^2$; and
    wherein the outer cover includes an initial amount of white space, wherein after all the active graphics present are activated, the surface area of white space on the outer cover changes by at least 15%, wherein the at least one active graphic is surrounded by the framing device or the outline and wherein the framing device or the outline has an inner perimeter that defines a surface area therein, all of the active graphics present occupying from about 35% to about 90% of the inner perimeter surface area of the framing device or the outline.

13. An absorbent article as defined in claim 12, wherein the at least one active graphic has a surface area of at least 1000 mm$^2$.

14. An absorbent article as defined in claim 12, wherein the at least one active graphic is visible from the exterior surface of the outer cover, the active graphic, once activated turning clear or to a white color and wherein the surface area of white space on the outer cover increases by at least 20% when all of the active graphics have been activated.

15. An absorbent article comprising:
    an outer cover having an interior surface and an exterior surface, the outer cover including a front region, a back region, and a crotch region positioned in between the front region and the back region, wherein the outer cover includes an initial amount of white space;
    an absorbent structure positioned adjacent the interior surface of the outer cover;

at least one active graphic that is incorporated into the absorbent article such that the active graphic is visible from the exterior surface of the outer cover; and a framing device that substantially surrounds the at least one active graphic, wherein the framing device is concentric with the at least one active graphic and highlights the at least one active graphic, the framing device comprising a permanent graphic and all of the active graphics having a total surface area of at least 800 $mm^2$, wherein more than 50% of the framing device is located in the crotch region, the framing device including an inner perimeter that defines a surface area contained therein, all the active graphics present occupying from about 35% to about 90% of the surface area contained within the inner perimeter of the framing device, wherein once the active graphics are activated, the amount of white space on the outer cover changes at least by 15%.

16. An absorbent article as defined in claim 15, wherein all of the active graphics together define a perimeter surface area and wherein the active graphic perimeter surface area covers at least 60% of the surface area within the inner perimeter of the framing device.

17. An absorbent article comprising:

an outer cover having an interior surface and an exterior surface, the outer cover including a front half and a back half, wherein the outer cover includes an initial amount of white space;

an absorbent structure positioned adjacent to the interior surface of the outer cover;

at least one active graphic incorporated into the absorbent article such that the at least one active graphic is visible from the exterior surface of the outer cover; and a framing device that substantially surrounds the at least one active graphic, wherein the framing device is concentric with the at least one active graphic and highlights the at least one active graphic, the framing device comprising a permanent graphic and all of the active graphics having a total surface area of at least 800 $mm^2$, the framing device including an outer perimeter that defines a surface area therein; and wherein the front half of the outer cover defines a printable surface area and wherein the surface area within the outer perimeter of the framing device occupies greater than about 10% of the printable surface area of the front half of the outer cover, and wherein the framing device has an inner perimeter that defines a surface area therein, all of the active graphics present occupying from about 35% to about 90% of the inner perimeter surface area of the framing device, wherein once the active graphics are activated, the amount of white space on the outer cover changes at least by 15%.

* * * * *